(12) United States Patent
Ruhland

(10) Patent No.: US 10,589,016 B2
(45) Date of Patent: Mar. 17, 2020

(54) TREATMENT SYSTEM WITH INFUSION APPARATUS PRESSURE PRIMING

(71) Applicant: GAMBRO LUNDIA AB, Lund (SE)

(72) Inventor: Daniel Ruhland, Roseville, MN (US)

(73) Assignee: Gambro Lundia AB, Lund (SE)

( * ) Notice: Subject to any disclaimer, the term of this patent is extended or adjusted under 35 U.S.C. 154(b) by 254 days.

(21) Appl. No.: 15/554,035

(22) PCT Filed: Apr. 12, 2016

(86) PCT No.: PCT/US2016/027061
§ 371 (c)(1),
(2) Date: Aug. 28, 2017

(87) PCT Pub. No.: WO2016/168162
PCT Pub. Date: Oct. 20, 2016

(65) Prior Publication Data
US 2018/0071450 A1 Mar. 15, 2018

Related U.S. Application Data

(60) Provisional application No. 62/147,889, filed on Apr. 15, 2015.

(51) Int. Cl.
*A61M 1/36* (2006.01)
*A61M 5/145* (2006.01)
(Continued)

(52) U.S. Cl.
CPC ........ *A61M 1/3672* (2013.01); *A61M 5/1456* (2013.01); *A61M 5/16804* (2013.01);
(Continued)

(58) Field of Classification Search
CPC .............. A61M 1/3672; A61M 1/3673; A61M 1/3675; A61M 1/3676; A61M 1/36;
(Continued)

(56) References Cited

U.S. PATENT DOCUMENTS

| 4,534,756 A | 8/1985 | Nelson |
| 4,710,163 A | 12/1987 | Butterfield |

(Continued)

FOREIGN PATENT DOCUMENTS

| EP | 0361793 | 4/1990 |
| EP | 1529546 | 5/2005 |

(Continued)

OTHER PUBLICATIONS

PCT/US2016/027061 International Search Report and Written Opinion dated Aug. 31, 2016 (16 pages).

(Continued)

*Primary Examiner* — Philip R Wiest
(74) *Attorney, Agent, or Firm* — Mueting, Raasch & Gebhardt, P.A.

(57) ABSTRACT

A system or method includes an infusion apparatus controllable to provide a fluid flow from a replaceable fluid dispenser at a set flow rate. The infusion apparatus may be commanded to operate on a replacement fluid dispenser to provide one or more boluses of the plurality of boluses into an infusion line. If the infusion apparatus is not being prevented (e.g., by system back pressure or frictional forces) from delivering the one or more boluses then the infusion apparatus may be controlled to deliver a plurality of boluses at a set flow rate. If the infusion apparatus is being prevented from delivering the one or more boluses then the infusion apparatus may be controlled to pressure prime the replacement fluid dispenser by accelerating one or more commands to the infusion apparatus to deliver one or more boluses into the infusion line.

24 Claims, 11 Drawing Sheets

(51) Int. Cl.
*A61M 5/168* (2006.01)
*G06F 19/00* (2018.01)
*A61M 5/142* (2006.01)

(52) U.S. Cl.
CPC ..... *G06F 19/3468* (2013.01); *A61M 5/14228* (2013.01); *A61M 2005/16863* (2013.01)

(58) Field of Classification Search
CPC .............. A61M 1/367; A61M 5/1456; A61M 5/16804; A61M 5/14228; A61M 2005/16863; G06F 19/3468
See application file for complete search history.

(56) References Cited

U.S. PATENT DOCUMENTS

| | | |
|---|---|---|
| 4,767,406 A | 8/1988 | Wadham |
| 4,846,792 A | 7/1989 | Bobo, Jr. |
| 4,898,576 A | 2/1990 | Philip |
| 4,959,050 A | 9/1990 | Witschi |
| 4,979,940 A | 12/1990 | Bobo, Jr. |
| 5,087,245 A * | 2/1992 | Doan ................ A61M 5/16859 128/DIG. 12 |
| 5,242,408 A | 9/1993 | Jhuboo |
| 5,295,967 A | 3/1994 | Rondelet |
| 5,356,378 A | 10/1994 | Doan |
| 5,423,743 A | 6/1995 | Butterfield |
| 5,647,853 A | 7/1997 | Feldman |
| 5,679,245 A | 10/1997 | Manica |
| 5,695,473 A | 12/1997 | Olsen |
| 5,762,805 A | 6/1998 | Truitt |
| 5,776,345 A | 7/1998 | Truitt |
| 5,803,712 A | 9/1998 | Davis |
| 5,910,252 A | 6/1999 | Truitt |
| 6,065,941 A | 5/2000 | Gray |
| 6,193,480 B1 | 2/2001 | Butterfield |
| 6,213,972 B1 | 4/2001 | Butterfield |
| 6,416,291 B1 | 7/2002 | Butterfield |
| 6,485,465 B2 | 11/2002 | Moberg |
| 6,572,604 B1 | 6/2003 | Platt |
| 6,648,861 B2 | 11/2003 | Platt |
| 7,306,736 B2 | 12/2007 | Collins |
| 7,517,332 B2 | 4/2009 | Tonelli |
| 7,744,553 B2 | 6/2010 | Kelly |
| 7,867,192 B2 | 1/2011 | Bowman |
| 7,998,111 B2 | 8/2011 | Moberg |
| 8,105,266 B2 | 1/2012 | Childers |
| 8,109,906 B2 | 2/2012 | Smisson, III |
| 8,182,461 B2 | 5/2012 | Pope |
| 8,267,881 B2 | 9/2012 | O'Mahony |
| 8,672,875 B2 | 3/2014 | Vanderveen |
| 8,764,408 B2 | 7/2014 | Smisson, III |
| 9,039,656 B2 | 5/2015 | Vanderveen |
| 9,138,537 B2 | 9/2015 | Miesel |
| 9,486,570 B2 | 11/2016 | Sternby |
| 9,579,452 B2 | 2/2017 | Adair |
| 2004/0133166 A1 | 7/2004 | Moberg |
| 2005/0131331 A1 | 6/2005 | Kelly |
| 2006/0184154 A1 | 8/2006 | Moberg |
| 2008/0154187 A1 | 6/2008 | Krulevitch |
| 2008/0281272 A1 | 11/2008 | Blundred |
| 2009/0012453 A1 | 1/2009 | Childers |
| 2010/0069841 A1 | 3/2010 | Miesel |
| 2012/0203195 A1 | 8/2012 | Pope |
| 2012/0245525 A1 | 9/2012 | Pope |
| 2014/0058351 A1 | 2/2014 | Pope |
| 2014/0188076 A1 | 7/2014 | Kamin |
| 2014/0194820 A1 | 7/2014 | Gray |
| 2014/0236119 A1 | 8/2014 | Tsoukalis |
| 2015/0005732 A1 | 1/2015 | Halbert |
| 2015/0374902 A1 * | 12/2015 | Chambers ............. A61M 5/142 73/168 |
| 2016/0331895 A1 | 11/2016 | Pope |

FOREIGN PATENT DOCUMENTS

| | | |
|---|---|---|
| EP | 1676527 | 7/2006 |
| EP | 2052683 | 4/2009 |
| EP | 2305334 | 4/2011 |
| EP | 1706160 | 3/2013 |
| JP | H06-154321 | 8/2001 |
| JP | 2009-521998 | 6/2009 |
| JP | 2012-521823 | 9/2012 |
| WO | WO 91/00113 | 1/1991 |
| WO | WO 96/08288 | 3/1996 |
| WO | WO 2004/057196 | 7/2004 |
| WO | WO 2007/141786 | 12/2007 |
| WO | WO 2010/046728 | 4/2010 |
| WO | WO 2012/151077 | 11/2012 |
| WO | WO 2013/004307 | 1/2013 |
| WO | WO 2014/099779 | 6/2014 |
| WO | WO 2014/105606 | 7/2014 |

OTHER PUBLICATIONS

PCT/US2016/027061 Preliminary Report on Patentability dated Oct. 26, 2017 (10 pages).
PCT/US2013/076400 Preliminary Report on Patentability dated Jul. 9, 2015 (14 pages).
PCT/US2013/076400 International Search Report and Written Opinion dated Mar. 27, 2014 (16 pages).
Office Action issued in Japan for Application No. 2017-553389 dated Nov. 15, 2019 (5 pages).

* cited by examiner

TREATMENT SYSTEM WITH INFUSION APPARATUS PRESSURE PRIMING

CROSS-REFERENCE

This application is a U.S. National Stage Application of International Application No. PCT/US2016/027061, filed Apr. 12, 2016 and published in English on Oct. 20, 2016 as International Publication No. WO 2016/168162 A1, which claims the benefit under 35 U.S.C. 119(e) of U.S. Provisional Application Ser. No. 62/147,889, filed on 15 Apr. 2015, which are all incorporated herein by reference in their entirety.

BACKGROUND

The disclosure herein relates to delivery of fluids from, for example, a fluid delivery system (e.g., an infusion apparatus with a connected replaceable fluid dispenser, such as a syringe). More particularly, the disclosure relates to pressure priming the infusion apparatus (e.g., in low flow rate fluid delivery instances).

Infusion devices are used for the delivery of medical fluids in various situations, e.g., such as the delivery of medical fluids for an extracorporeal blood circuit, drug infusion, etc. For example, infusion devices may be usefully applied for infusing an anticoagulant in an extracorporeal circuit operatively associated with a machine for extracorporeal blood treatment. Such extracorporeal treatments may include removal of blood from the patient, external treatment thereof away from the human body, followed by its return to the patient. For example, extracorporeal blood may be made to circulate through a blood circuit comprising, in general, an arterial line, or blood removal line, which takes the blood from the patient to a blood treatment device (e.g., a dialyzer filter) and a venous line, or blood return line, which returns the treated blood to the patient.

To reduce the risk of coagulation of the extracorporeal blood, infusion of an anticoagulant, such as heparin, for example, into the extracorporeal circuit may be used (e.g., generally into the arterial line, through an infusion line connected pre-filter, with relatively low infusion flow rates). An infusion device that may be used, for example, to deliver the anticoagulant may include an actuation apparatus operating on a fluid dispenser, such as a syringe. For example, the actuation apparatus may include a pushing element, operable on command of a linear actuator, to push or displace a plunger of a syringe containing the anticoagulant at an advancement rate which is predetermined (e.g., relatively slow). For example, in a dialysis treatment, the syringe may contain a quantity of anticoagulant necessary for several hours of treatment. The pushing element and the actuator may be part of the extracorporeal treatment machine (e.g., a dialysis machine), while the syringe may be of the single-use type (e.g., a disposable or replaceable fluid dispenser).

Likewise, alternatively, to reduce the risk of coagulation of the extracorporeal blood, an anticoagulant, such as a citrate, for example, provided into the extracorporeal circuit may be used (e.g., generally provided, pre-filter, into the arterial line as a function of blood flow rate). In the case of regional citrate anticoagulation, an infusion device (e.g., including a replaceable fluid dispenser) may be used, for example, to deliver a fluid including calcium into the extracorporeal circuit (e.g., generally into the return line, through an infusion line connected post-filter, with relatively low infusion flow rates, or directly into the patient via a venous line with relatively low infusion flow rates).

Various configurations of such extracorporeal treatment machines or systems, as well as other apparatus that employ infusion devices, may include components and/or operational parameters that present a pressure and/or stiffness which operate against the delivery of fluid from the infusion apparatus. One or more of the pressures operating against fluid flow from an infusion apparatus may be monitored in the system (e.g., pressures measured at a pre-filter position in the system, measured at the return line, etc.). When a fluid dispenser (e.g., syringe) of an infusion apparatus is replaced during operation by a replacement fluid dispenser (e.g., a replacement syringe), such pressures and/or stiffness which operate against the delivery of fluid may prevent delivery of fluid into the system from the replacement fluid dispenser for an undesirable length of time (e.g., due to use of a relatively low infusion flow rate).

SUMMARY

The present disclosure describes systems and methods that may be used to pressure prime a fluid dispenser (e.g., a syringe) of an infusion apparatus to decrease the amount of time before boluses from the syringe are successfully delivered into an infusion line after a replacement fluid dispenser is connected in the infusion apparatus (e.g., especially when the rate of delivering such boluses is low).

In one exemplary embodiment of a blood treatment system that provides such pressure priming, the system includes a blood pump, a filter (e.g., wherein access and return blood lines are in fluid communication with the filter), and an infusion line configured to be connected in fluid communication to one of the access blood line, the return blood line, and a patient. The system may also include an infusion apparatus controllable to provide a fluid flow from a replaceable fluid dispenser at a set flow rate (e.g., wherein the fluid flow may include a plurality of boluses) and the infusion apparatus may include an actuator configured to operate on the replaceable fluid dispenser to provide one bolus of the plurality of boluses into the infusion line when commanded. Further, the system may include a controller configured to determine, upon connection of a replacement fluid dispenser in the infusion apparatus, if the infusion apparatus is being prevented when commanded from delivering one or more boluses to one of the access blood line, the return blood line, and the patient (e.g., if a system back pressure operating on the replacement fluid dispenser and/or a frictional force associated with the replacement fluid dispenser is preventing the infusion apparatus when commanded from delivering one or more boluses to one of the access blood line, the return blood line, and the patient), and to prime the pressure in the replacement fluid dispenser if it is determined that the infusion apparatus is being prevented from delivering one or more boluses to one of the access blood line, the return blood line, and the patient. For example, the controller may be configured to prime the pressure in the replacement fluid dispenser by accelerating one or more commands to the infusion apparatus to deliver one or more boluses into the infusion line so that pressure in the replacement fluid dispenser increases and a time required to deliver boluses to one of the access blood line, the return blood line, and the patient is decreased (e.g., a time interval between an accelerated command and a prior command immediately preceding the accelerated command may be less than a time interval between commands provided to deliver boluses at the set flow rate).

One exemplary method to control delivery of a fluid flow from an infusion apparatus in a blood treatment system is also provided (e.g., wherein the fluid flow may include a plurality of boluses). The method may include connecting a replacement fluid dispenser in the infusion apparatus to replace a prior replaceable fluid dispenser, commanding the infusion apparatus to operate on the replacement fluid dispenser to provide one or more boluses of the plurality of boluses into an infusion line, and determining if the infusion apparatus is being prevented when commanded from delivering the one or more boluses to one of the access blood line, the return blood line, and the patient (e.g., determining if a system back pressure operating on the replacement fluid dispenser and/or a frictional force associated with the replacement fluid dispenser is preventing the infusion apparatus when commanded from delivering one or more boluses to one of the access blood line, the return blood line, and the patient). The infusion apparatus may be controlled to deliver a plurality of boluses at a set flow rate into the infusion line if the infusion apparatus is not being prevented from delivering the one or more boluses and the replacement fluid dispenser may be pressure primed if the infusion apparatus is being prevented from delivering the one or more boluses. For example, the replacement fluid dispenser may be pressure primed by accelerating one or more commands to the infusion apparatus to deliver one or more boluses into the infusion line such that pressure in the replacement fluid dispenser increases and a time required to deliver boluses to one of the access blood line, the return blood line, and the patient is decreased (e.g., wherein a time interval between an accelerated command and a prior command immediately preceding the accelerated command may be less than a time interval between commands provided to deliver boluses at the set flow rate).

Another exemplary treatment system may include an infusion line and an infusion apparatus controllable to provide a fluid flow from a replaceable fluid dispenser at a set flow rate downstream therefrom (e.g., wherein the fluid flow may include a plurality of boluses, and further wherein the infusion apparatus may include an actuator configured to operate on the replaceable fluid dispenser to provide one bolus of the plurality of boluses into the infusion line when commanded). The system may further include a controller configured to determine, upon connection of a replacement fluid dispenser in the infusion apparatus, if the infusion apparatus is being prevented when commanded from delivering one or more boluses downstream of the infusion apparatus, and prime the pressure in the replacement fluid dispenser if it is determined that the infusion apparatus is being prevented from delivering one or more boluses downstream of the infusion apparatus (e.g., wherein the controller may be configured to prime the pressure in the replacement fluid dispenser by accelerating one or more commands to the infusion apparatus to deliver one or more boluses into the infusion line so that pressure in the replacement fluid dispenser increases and a time required to deliver boluses is decreased, and wherein a time interval between an accelerated command and a prior command immediately preceding the accelerated command may be less than a time interval between commands provided to deliver boluses at the set flow rate).

Another exemplary method to control delivery of a fluid flow from an infusion apparatus (e.g., wherein the fluid flow may include a plurality of boluses) may include connecting a replacement fluid dispenser in the infusion apparatus to replace a prior replaceable fluid dispenser; commanding the infusion apparatus to operate on the replacement fluid dispenser to provide one or more boluses of the plurality of boluses into an infusion line; determining if the infusion apparatus is being prevented when commanded from delivering the one or more boluses downstream of the infusion apparatus; controlling the infusion apparatus to deliver a plurality of boluses at a set flow rate into the infusion line if the infusion apparatus is not being prevented from delivering the one or more boluses; and pressure priming the replacement fluid dispenser if the infusion apparatus is being prevented from delivering the one or more boluses (e.g., such as due to a downstream pressure) by accelerating one or more commands to the infusion apparatus to deliver one or more boluses into the infusion line such that pressure in the replacement fluid dispenser increases and a time required to deliver boluses is decreased (e.g., wherein a time interval between an accelerated command and a prior command immediately preceding the accelerated command may be less than a time interval between commands provided to deliver boluses at the set flow rate).

One or more embodiments of the methods and/or systems may include one or more of the following features and/or processes: the controller may be configured for or the method may include controlling the infusion apparatus to deliver a plurality of boluses at the set flow rate into the infusion line upon delivering a predetermined number of boluses resulting from accelerated commands; the controller may be further configured to or the method may further include increasing the pressure in the replacement fluid dispenser by attempting to provide boluses at a rate greater than the set flow rate; and determining whether the infusion apparatus is being prevented from delivering one or more boluses may include determining whether the infusion line appears occluded.

In one or more embodiments of the systems and/or methods, each bolus may be associated with a measurable force response over time, and further, determining whether the infusion line appears occluded may be based on the measurable force response over time. For example, determining whether the infusion line appears occluded may include receiving a force signal representative of a measurable force response associated with a bolus, determining an integrated force response value using integration of the force signal over a predetermined time period, providing a ratio corresponding to the bolus between the integrated force response value and a normalizing value, and determining if the infusion line appears occluded based at least on the ratio corresponding to the bolus. Further, alone or in combination therewith, determining whether the infusion line appears occluded may include receiving a force signal representative of a measurable force response for each of at least two boluses, determining a slope based on a force value taken at a predetermined time during each measurable force response for each of the at least two boluses indicative of the stiffness of at least the replacement fluid dispenser, and determining if the infusion line appears occluded based at least on the slope.

Further, one or more embodiments of the methods and/or systems may include one or more of the following features and/or processes: the controller of the system may be further configured for or the method may further include comparing a calculated volume of fluid that was expected to be delivered based at least on actuator displacement of an actuator of the infusion apparatus since the time of connection of the replacement fluid dispenser in the infusion apparatus to a predetermined volume of the replacement fluid dispenser and preventing or allowing pressure priming based on the comparison; and/or the controller of the system may be further configured for or the method may further include comparing a pressure of the replacement fluid dispenser to at least one of a measurable pressure at an inlet of the filter, a measurable pressure of the return blood line, or a zero pressure (or any other downstream pressure) and preventing or allowing pressure priming based on the comparison.

Still further, in one or more embodiments of the systems and/or methods, the controller of the system may be further configured for or the method may further include commanding the infusion apparatus to attempt to deliver one or more boluses into the infusion line based on the set flow rate upon connecting the replacement fluid dispenser in the infusion apparatus. If it is determined that the infusion apparatus is not being prevented when commanded from delivering one or more boluses, e.g., to one of the access blood line, the return blood line, and the patient then the infusion apparatus continues to be commanded to deliver further boluses as prescribed by the set flow rate, and further, if it is determined that the infusion apparatus is being prevented when commanded from delivering the one or more boluses, e.g., to one of the access blood line, the return blood line, and the patient then the infusion apparatus is commanded to deliver one or more boluses at an accelerated rate greater than the set flow rate.

Still further, in one or more embodiments of the systems and/or methods, the controller of the system may be further configured for or the method may further include commanding the infusion apparatus to deliver a bolus into the infusion line based on the set flow rate upon connecting the replacement fluid dispenser in the infusion apparatus. If it is determined that the infusion apparatus is not being prevented when commanded from delivering the bolus, e.g., to one of the access blood line, the return blood line, and the patient then the infusion apparatus continues to be commanded to deliver further boluses at time intervals from immediately preceding boluses as prescribed by the set flow rate, and further, if it is determined that the infusion apparatus is being prevented when commanded from delivering the bolus, e.g., to one of the access blood line, the return blood line, and the patient then the infusion apparatus is commanded to accelerate a command to deliver a next bolus at a time interval from the immediately preceding command that is less than the time interval as prescribed by the set flow rate. Still further, for example, until a predetermined number of boluses have been delivered, e.g., to one of the access blood line, the return blood line, and the patient accelerated commands may continue to be provided to the infusion apparatus.

Yet further, any one or more embodiments of the methods and/or systems may include one or more of the following features and/or processes: the replacement fluid dispenser connected in the infusion apparatus may be connected in the infusion apparatus upon determination that a replaceable fluid dispenser change was needed during operation of the treatment system; the set flow rate may be a low infusion rate (e.g., wherein the time interval between commands provided to deliver boluses at the set flow rate is greater than 45 seconds); the time interval between an accelerated command and a prior command immediately preceding the accelerated command may be equal to or less than ½ the time interval between commands provided to deliver boluses at the set flow rate; the time interval between an accelerated command and a prior command immediately preceding the accelerated command may be equal to or less than ¼ the time interval between commands provided to deliver boluses at the set flow rate; the replacement fluid dispenser may be a syringe; and/or the infusion apparatus may be configured to deliver an anticoagulant or a fluid used in combination with an anticoagulant.

Another exemplary blood treatment system may include a blood pump, a filter (e.g., wherein access and return blood lines are in fluid communication with the filter), an infusion line, and a user interface configured to allow a user to provide an input that may be a selected connection (e.g., wherein the selected connection may include one of a connection of the infusion line to the return blood line or connection of the infusion line directly to a patient). The system may further include an infusion apparatus controllable to provide a fluid flow from a replaceable fluid dispenser at a set flow rate to the infusion line (e.g., the fluid flow may include a plurality of boluses) and a controller configured to determine (e.g., upon connection of a replacement fluid dispenser in the infusion apparatus and if the user provided a selected connection of the infusion line to the return blood line) whether the infusion apparatus is being prevented from delivering one or more boluses to the return blood line, and to prime the pressure in the replacement fluid dispenser if it is determined that the infusion apparatus is being prevented from delivering one or more boluses to the return blood line.

In one or more embodiments of the system, the controller may be further configured to determine (e.g., upon connection of a replacement fluid dispenser in the infusion apparatus and if the user provided a selected connection of the infusion line to the patient) whether a frictional force associated with the replacement fluid dispenser is preventing the infusion apparatus from delivering one or more boluses into the infusion line, and to prime the pressure in the replacement fluid dispenser if it is determined that the frictional force associated with the replacement fluid dispenser is preventing the infusion apparatus from delivering one or more boluses to the patient. For example, further, the replacement fluid dispenser may include a syringe configured to deliver a fluid for use in combination with a citrate anticoagulant.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

BRIEF DESCRIPTION OF THE DRAWING

FIG. 5 is a block diagram illustrating another exemplary algorithm for use in pressure priming of an infusion apparatus for delivery of a fluid which may be implemented by a system, for example, such as shown generally in

FIG. 3.

DETAILED DESCRIPTION OF EXEMPLARY EMBODIMENTS

Figure 1:
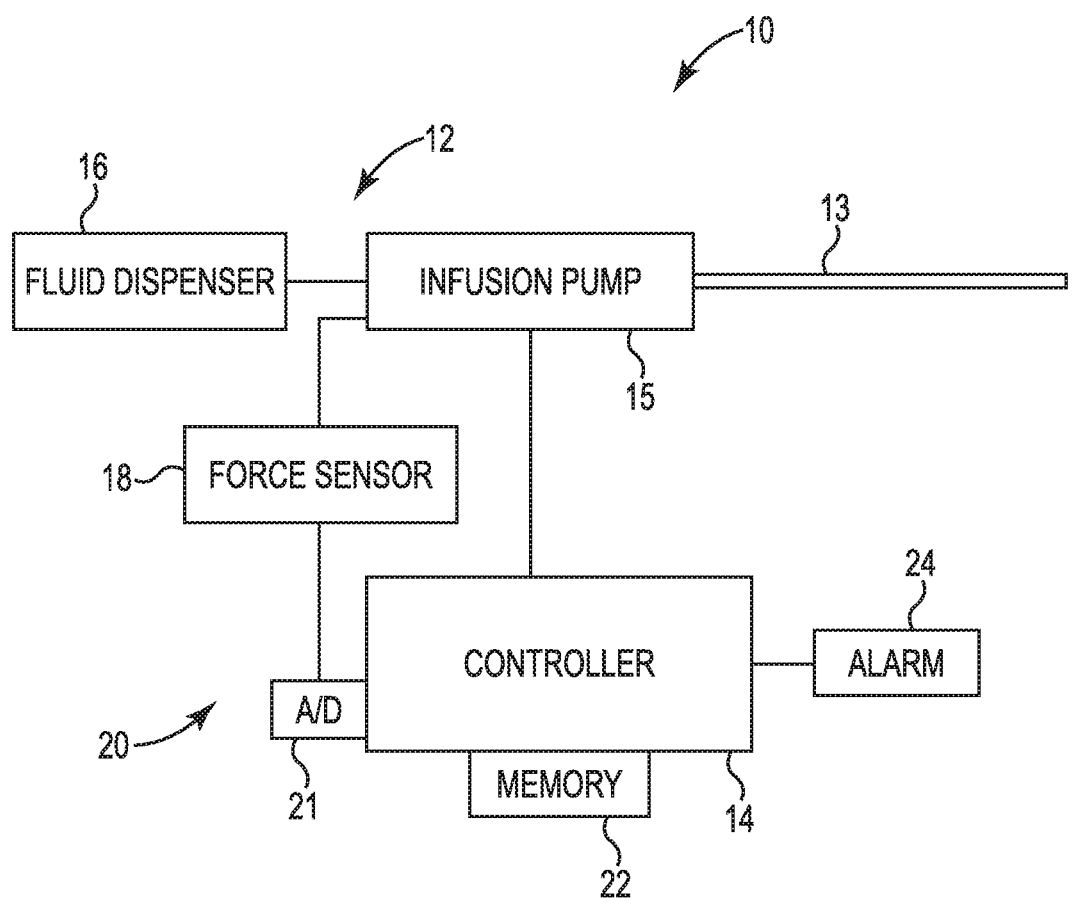
FIG. 1 is a simplified block diagram of an exemplary fluid delivery system for the delivery of fluids by an infusion apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and apparatus for use in the pressure priming a replacement fluid dispenser (e.g., syringe) of an infusion apparatus (e.g., an infusion apparatus including an actuation apparatus, such as a pushing element, operable on command of an actuator, such as a linear actuator, to push or displace a plunger of a syringe containing an anticoagulant or a fluid for use in combination with an anticoagulant) to provide delivery of a fluid flow including a plurality of boluses shall be described with reference to FIGS. 1-11. For example, the infusion apparatus may be controllable to provide a fluid flow from a replaceable fluid dispenser at a set flow rate (e.g., a flow rate set during setup by user input or adjusted during treatment by user input) using an actuator configured to operate on the replaceable fluid dispenser to provide one bolus of the plurality of boluses into the infusion line when commanded as will be further described herein with reference to FIGS. 1-2. Although not limited such medical devices and/or systems, the infusion apparatus may be part of a medical device or system (e.g., a blood treatment system) that includes a blood pump, a filter (e.g., wherein access and return blood lines are in fluid communication with the filter as part of the blood circuit), and an infusion line that is in fluid communication with one of the access blood line, return blood line, and a patient, such as shown and described with reference to FIG. 3.

For example, the infusion apparatus may be provided as part of the medical treatment system to provide a fluid associated with anticoagulation functionality. For example, to provide for different types of anticoagulation functionality, the infusion line may be connected at one or more different locations in the medical treatment system. For example, if heparin is used as an anticoagulant in the performance of a blood treatment, the infusion line is generally connected pre-filter in the arterial line or access line to provide a heparin infusion line connection. If, for example, a citrate anticoagulant (e.g., in regional citrate anticoagulation) is used to provide anticoagulation functionality in the performance of the blood treatment, the infusion line is generally connected to provide infusion of a fluid including calcium at a post-filter location. For example, the infusion line may be connected post-filter in the return line to provide a calcium infusion line connection or the infusion line may be connected directly to the patient undergoing treatment to provide the calcium infusion line connection.

During a blood treatment of a patient, the replaceable fluid dispenser (e.g., syringe) connected in the infusion apparatus may become empty and require replacement. In such a case, appropriate lines are clamped, the replaceable fluid dispenser (e.g., syringe) is removed, and the replacement fluid dispenser (e.g., syringe) is connected, or otherwise coupled, in the infusion apparatus. Any clamps on lines would then be removed and operation continued.

For example, in order for fluid to flow from the replacement fluid dispenser (e.g., syringe) when in heparin mode, the pressure in the syringe must exceed the filter pressure (e.g., since it is connected pre-filter), and, also an additional cracking pressure of a one-way valve (e.g., if such a one way valve is used in the syringe pump set configuration to prevent the backflow blood into the syringe due to peristaltic pump action) to deliver one or more boluses into the infusion line. The filter pressure can vary widely depending on the operating point of the blood pump and fluid pumps used in the blood treatment system. Similarly, when the infusion apparatus is used in a calcium mode (e.g., in association with a citrate anticoagulation process) and the infusion line is connected to the return line, the syringe pressure must exceed the return pressure to deliver one or more boluses into the infusion line. Yet still further, similarly, when the infusion apparatus is used in a calcium mode (e.g., in association with a citrate anticoagulation process) and the infusion line is connected directly to the patient, the syringe pressure must still exceed any resistance due to the cracking pressure of a one-way valve of the infusion line (e.g., if such a one way valve is used in the syringe pump set configuration); actual patient backpressure where the height difference between the patient connection relative to the syringe is a component of the backpressure; and frictional forces (e.g., frictional drag) associated with the syringe (e.g., where syringe pressure builds only after overcoming the frictional component characteristics between the syringe plunger and barrel).

In other words, measurable pressure components and unmeasurable components may operate on the replacement fluid dispenser (e.g., syringe) and prevent the infusion apparatus when commanded from delivering one or more boluses into the infusion line. For example, one or more different measurable or unmeasurable components may include the pressure at the inlet of the filter of the blood treatment system, the pressure at the return line of the blood treatment system, the cracking pressure of one-way valves used in the blood treatment system, the frictional characteristics and/or other characteristics of components or fluids (e.g., stiffness of a syringe or frictional drag forces between the syringe plunger and barrel), etc.

For example, when the replacement fluid dispenser (e.g., syringe) is connected pre-filter in heparin mode, the infusion apparatus may be prevented from delivering boluses into the blood circuit by one or more of the back pressure defined by the filter pressure (e.g., a pressure measurable at the filter inlet), the cracking pressure of a one-way valve (e.g., if such a one way valve is used), the frictional forces associated with the syringe or syringe stiffness, etc. Similarly, when the infusion apparatus is used in a calcium mode (e.g., in association with a citrate anticoagulation process) and the infusion line is connected to the return line, the infusion apparatus may be prevented from delivering boluses into the blood circuit by one or more of the back pressure operating on the fluid dispenser defined by the return pressure (e.g., measurable in the return line), the frictional forces associated with the syringe or syringe stiffness, etc. Still further, when the infusion apparatus is used in a calcium mode and the infusion line is connected directly to the patient, the infusion apparatus may be prevented from delivering boluses to the patient by one or more of the cracking pressure of a one-way valve of the infusion line (e.g., if such a one way valve is used in the syringe pump set configuration), the actual patient backpressure where the height difference between the patient connection relative to the syringe is a component of the backpressure; and the frictional component characteristics between the syringe plunger and barrel or syringe stiffness, etc.

If a back pressure and/or a frictional component is present and operating on the replacement fluid dispenser to prevent the infusion apparatus when commanded from delivering one or more boluses to one of the access blood line, the return blood line, and the patient, a pressure priming algorithm may be used to increase the pressure in the replacement fluid dispenser and/or overcome the frictional component and decrease the time required to deliver boluses to one of the access blood line, the return blood line, and the patient. For example, pressure priming may include an algorithm to pressurize the syringe, after a syringe change, to the level of the filter or return pressure in order to achieve flow in a timely manner. For example, in heparin mode, the syringe infusion line is connected pre-filter. The filter pressure represents the pressure at the inlet to the filter. This pressure is a function of dialysis filter flow resistance, the return line and catheter, and the blood viscosity.

For example, if it is determined that the infusion apparatus is being prevented from delivering one or more boluses to one of the access blood line, the return blood line, and the patient, then pressure priming may be used to increase the pressure in the replacement fluid dispenser. The pressure in the fluid dispenser may be primed by accelerating one or more commands to the infusion apparatus to deliver one or more boluses into the infusion line so a time required to deliver boluses to one of the access blood line, the return blood line, and the patient is decreased (e.g., the pressure in the replacement fluid dispenser is increased at a more rapid rate, the frictional forces associated with the syringe are overcome more quickly, etc.). For example, a time interval between an accelerated command and a prior command immediately preceding the accelerated command may be less than a time interval between commands provided to deliver boluses at a set flow rate (e.g., the flow rate set for the treatment and at which the infusion apparatus is supposed to be delivering the plurality of boluses). If the infusion apparatus is not being prevented when commanded from delivering one or more boluses to one of the access blood line, the return blood line, and the patient, then boluses may be delivered according to a set flow rate for the treatment.

Pressure priming may be of particular benefit at low flow rates. For example, the pressure priming algorithm may include, for low flow rates, that if delivery of a micro-bolus looks occluded (e.g., delivery into the blood circuit is prevented) then the next one may be accelerated (e.g., another micro-bolus is commanded early (such as within 45 seconds after the last one) rather than waiting a much longer time period in accordance with a set flow rate that is low), and/or such acceleration of commanded boluses may continue to be accelerated up to the point where flow is established to one of the access blood line, the return blood line, and the patient.

Figure 3:
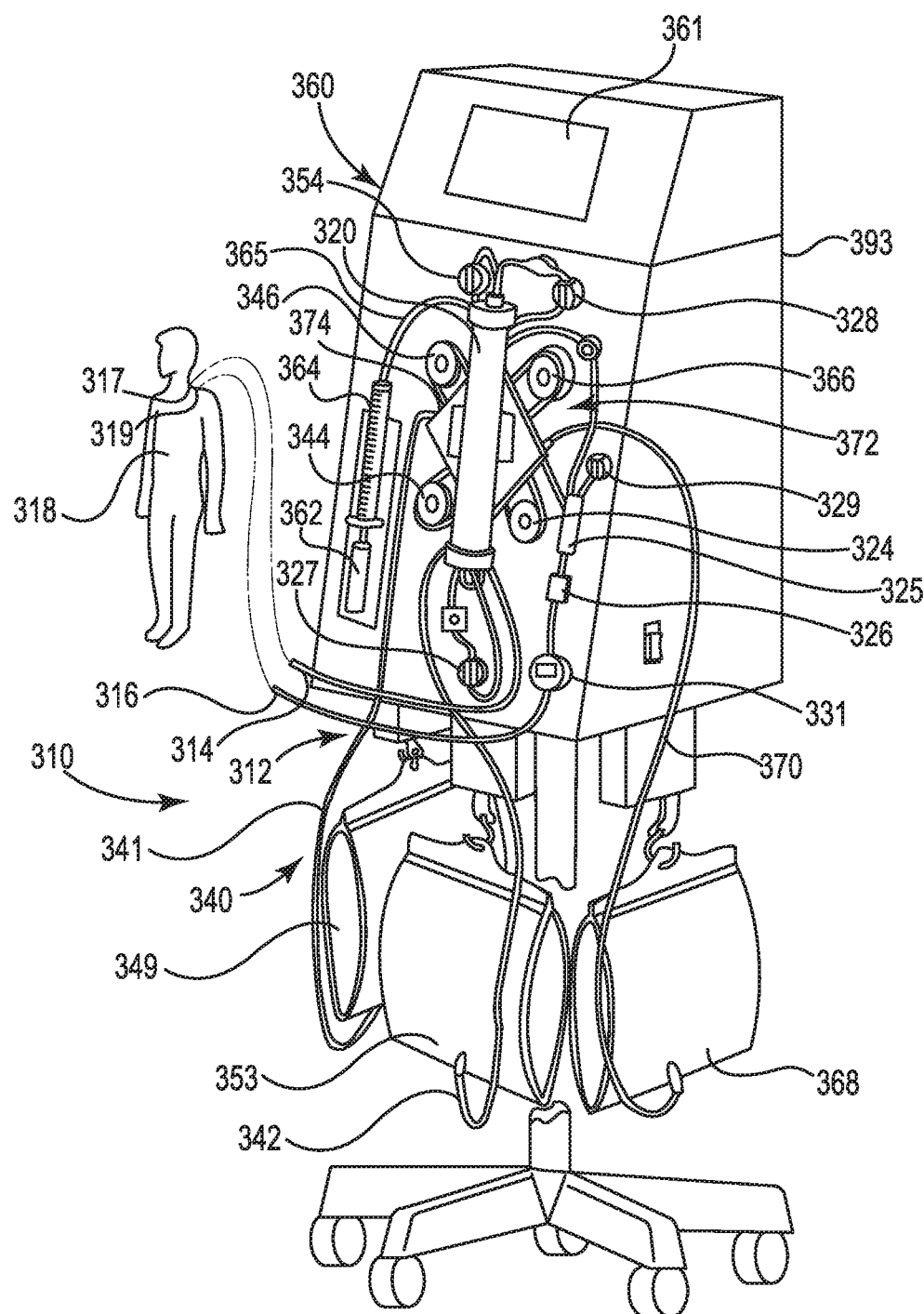
FIG. 3 is a perspective view of an exemplary extracorporeal blood treatment apparatus or machine that may include pressure priming functionality described herein.

FIG. 1 shows one general exemplary embodiment of a fluid delivery system 10 for use in providing a fluid flow by an infusion apparatus 12 (e.g., a plurality of boluses from a fluid dispenser 16 delivered by an infusion pump 15, or other infusion and/or actuation apparatus, into an infusion line 13 of a circuit, for example, such as delivery of fluid in small boluses (e.g., micro-boluses) into a line of an extracorporeal blood circuit of an extracorporeal blood treatment apparatus, such as generally shown in FIG. 3). The fluid flow may be delivered by the infusion apparatus 12 under control of controller 14 provided with an input from force sensor 18 (e.g., via an analog to digital (A/D) converter 21), as well as other control inputs (e.g., such as displacement sensors of an actuator for the infusion apparatus, etc.). The controller 14 is associated with memory 22 for use in carrying out the functionality as described herein. For example, an actuator of the infusion pump 15 may be configured to operate on the replaceable fluid dispenser 16 to provide one bolus of a plurality of boluses into the infusion line 13 when commanded by the controller 14. For example, the infusion apparatus 12 may be commanded by the controller 14 to deliver a plurality of boluses into the infusion line 13 at a set flow rate. Further for example, as described herein, pressure priming of a replacement fluid dispenser 16 may be carried out by the controller 14 accelerating one or more commands to the actuator to attempt to deliver one or more boluses into the infusion line 13. However, if a back pressure on the fluid dispenser 16 prevents delivery of such boluses into the infusion line 13, pressure in the fluid dispenser 16 increases. Further, monitoring system 20 including, e.g., the force sensor, may include an alarm 24 for providing an alarm indication when an abnormal condition or occlusion is detected.

Generally, in one or more embodiments described, the system 10 includes infusion apparatus 12 (e.g., a syringe pump) which under control of controller 14 may provide a fluid flow at an infusion flow rate (e.g., using an infusion command pattern to control the pump to deliver small boluses from a syringe, for example, at a set flow rate). The infusion apparatus 12 is associated with a force sensor 18 configured to provide a force signal to controller 14 representative of the fluid flow being delivered by infusion apparatus 12. The controller 14 is further configured to control the infusion apparatus 12 to intermittently deliver a defined volume or bolus of fluid in the fluid flow (e.g., a drive system of the syringe pump may be actuated to move the syringe plunger in small steps; each step producing a small bolus infusion into the infusion line 13). Each of such perturbations or boluses of the fluid flow may result in a measurable force response (e.g., measurable over time by force sensor 18). The resulting measurable force response may include at least a maximum force associated therewith.

The infusion apparatus 12 may be any suitable apparatus for delivering a fluid flow. For example, such infusion apparatus may include a syringe pump, such as, for example, described herein, or any other infusion apparatus that includes an actuator (e.g., a linear displacement actuator, or any displacement actuator) that operates upon a replaceable fluid dispenser to deliver a plurality of boluses into an infusion line. Further, for example, any infusion pump may benefit from the techniques described herein at low flow rates (e.g., such as those connected to a configuration where the backpressure varies significantly and/or where a one way valve is in the connection between the syringe and the downstream backpressure).

Figure 2:
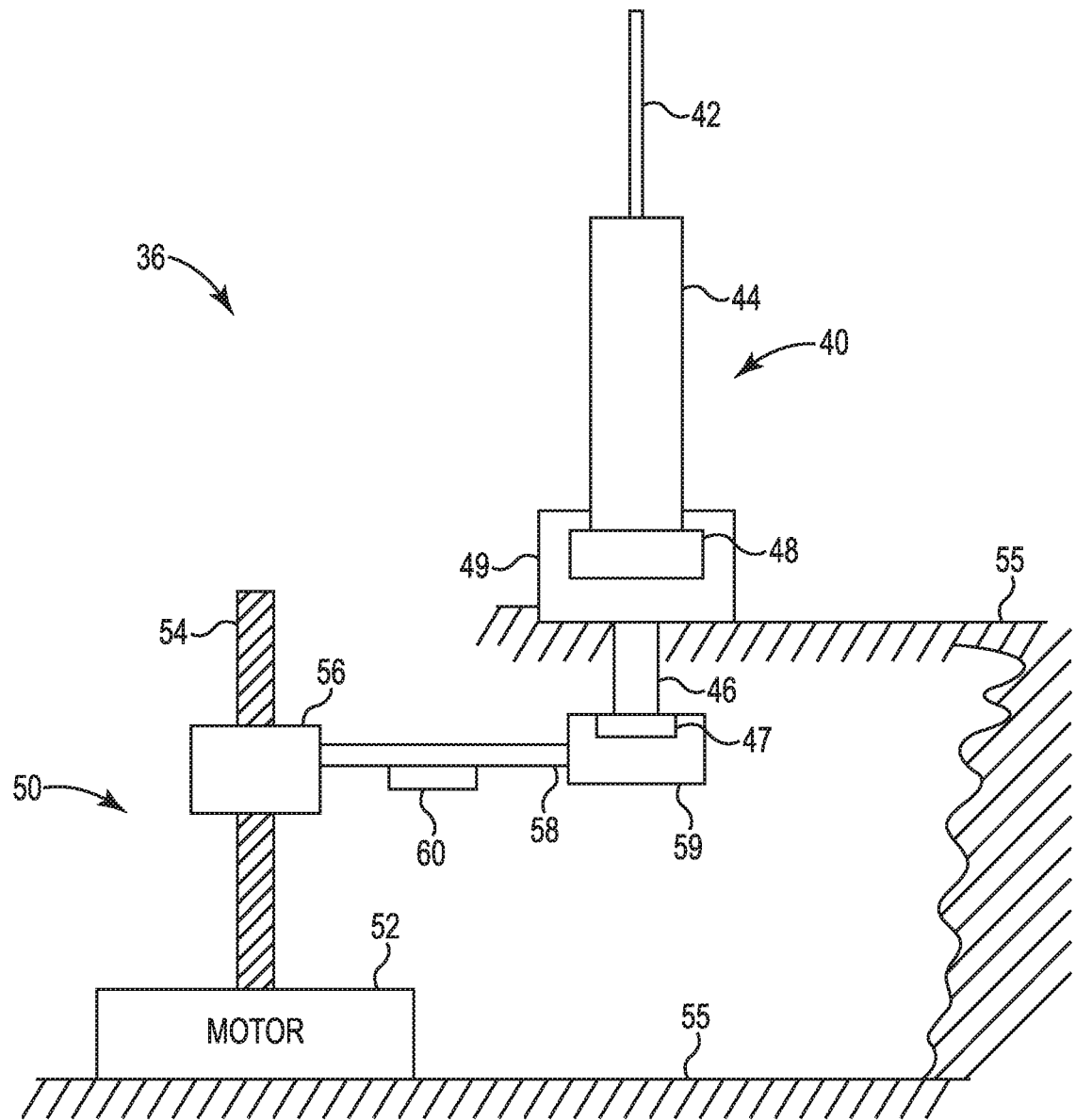
FIG. 2 is an illustration of an exemplary infusion apparatus such as shown generally in FIG. 1.

One exemplary infusion apparatus 36 (e.g., a syringe pump) is shown in FIG. 2. For example, as shown therein, the exemplary infusion apparatus 36 may be disposed on a housing such as shown generally by the reference numeral 55 (e.g., mounted on a panel of a machine or apparatus such as shown in FIG. 3). For example, the housing 55 may be configured to receive a replaceable syringe 40 containing a fluid to be delivered thereby (e.g., an anticoagulant to be delivered into an extracorporeal blood circuit, a drug to be delivered to a patient to treat a medical condition, a fluid including calcium as used in citrate anticoagulation, etc.). For example, the syringe 40 may include a fluid reservoir portion 44 to hold a fluid to be delivered and a coupling portion 48 that is fixedly mountable to the housing 55. Any suitable manner of affixing the coupling portion 48 and/or one or more other non-movable portions of the syringe 40 to the housing 55 may be used. For example, the fixing of the coupling portion 48 to the housing 55 may be provided with use of a syringe clamping or retaining structure 49 allowing the syringe to be affixed to housing 55 and later removed (e.g., the replaceable syringe being disposable, reusable, capable of being sterilized, etc.).

Further, for example, the syringe 40 includes a plunger 46. The plunger 46 may include a first end positionable (e.g., movable) within the fluid reservoir portion 44 (or barrel) and a second end 47. The plunger 46 may be moved within the fluid reservoir portion 44 to provide a fluid flow to a connected infusion line 42 (e.g., a line for infusion of anticoagulant which is coupled or terminates in an arterial line; or a calcium infusion line which is coupled or terminates in the return line or is directly connected to a patient).

The infusion apparatus 36 may further include an actuator 50 to control movement of the plunger 46 of the syringe 40. The actuator 50 may be any suitable actuator capable of controlling movement of the plunger 46. For example, the actuator 50 may be a linear actuator that includes a mobile portion 56 (e.g., movable along a straight movement direction). The mobile portion 56 may include a pushing structure 58 to interact with (e.g., have contact with or be coupled to) the plunger 46 (e.g., at the plunger end 47) to exert a pushing force thereon as the mobile portion 56 is moved for causing infusion of fluid from the fluid reservoir portion 44 into line 42. Further, for example, the mobile portion 56 of the actuator 50 may be guided by an endless screw translator 54 rotated by an electric motor 52, for example, a step motor, to move the mobile portion 56, and as such the pushing structure 58, to apply the push force on the plunger 46. The motor 52 and the syringe retaining structure 49 are generally fixed to the same structure such that movement of the mobile portion 56 (e.g., truck) and pushing structure 58 (e.g., structure that may include a plunger clip 59 configured to capture the plunger end 47) may suitably move plunger 46.

The infusion apparatus 36 may further comprise a force sensor 60 to measure a push force applied on the pushing structure 58. Any suitable force sensor may be used, such as, for example, one or more load cells, strain gauges, piezo-electric force sensor, torque controlled driving motor, etc. In one or more embodiments, the force sensor 60 may include an analog transducer of force (e.g., a load cell) which may continuously measure the pushing force applied on the pushing structure 58. Such a measured force may be an indirect measurement of the syringe pressure for the fluid being infused (e.g., the pressure may be calculated based thereon). For example, in the illustrative embodiment of FIG. 2, the force sensor 60 may be arranged between the linearly moveable mobile portion 56 and the pushing structure 58 (e.g., structure in contact with plunger 46). In other words, the force sensor 60 enables a measurement to be taken of the force applied on the plunger 46 of the syringe 40, and provide a measurable for response as described herein.

The syringe pressure may be estimated using the force sensed at the syringe and by making an inexact assumption about the amount of frictional drag force lost to overcome friction between the syringe plunger and barrel. For example, the frictional drag force may vary between syringes depending on the syringe construction and manufacturing tolerances, and even at different plunger positions within the same syringe. For example, the frictional drag force may vary from 1 newton (N) to 20 N. One may use a force of 4 N for the frictional drag force when computing estimated syringe pressure from sensed force. For example, the estimate of syringe pressure is then: $P=7500.615*(F-4)/A$; where P is estimated syringe pressure in mmHg, F is sensed force in newtons (N), and A is the syringe cross sectional area in millimeters squared (cross sectional area of the barrel). Therefore, a syringe pressure of the fluid being infused may be measured indirectly; for example, indirectly measured or estimated using a force sensor associated with the infusion apparatus. One will recognize that it may be possible to directly measure such pressure as well. As such, as used herein, due to the relationship between the syringe pressure and the force measured representative thereof, such terms may be used interchangeable herein.

One will recognize that various actuator configurations may be used to provide the push force on the plunger 46, as well as to measure the force, and that the present description is not limited to any particular configuration. For example, the infusion apparatus 36 may include other sensors, such as a sensor for measuring the displacement (e.g., displacement measuring device, visual sensor for capturing displacement, or any other sensor suitable to measure displacement) of the mobile portion 56 of the linear actuator (e.g., including the pushing structure 58) so as to determine the distance over which the drive system or actuator moves the structure that moves the plunger (e.g., which may include a plunger clip that is configured to capture the plunger), may include various types of coupling structures (e.g., holding structures, clamping structures, etc.) to provide the coupling of the various components, etc.

Further, although the present description is primarily provided with respect to a syringe pump, such as described herein, and syringe pumps which are described in various documents including, for example, U.S. Pat. No. 7,517,332 to Tonelli et al., entitled "Infusion Device For Medical Fluids" (e.g., which is incorporated by reference herein), one will recognize that the pressure priming algorithms provided herein may be suitable for use with various other types of infusion apparatus, for example, which use replaceable fluid dispensers.

With further reference to FIG. 1, the controller 14 may include any controller suitable to implement the functionality described herein, including the pressure priming functionality associated with providing fluid flow by infusion apparatus 12. In one or more embodiments, the controller 14 commands the infusion apparatus 12 to deliver a fluid flow into line 13 (e.g., commands the actuator 50 of the infusion apparatus 36 each time the apparatus is to deliver a bolus of fluid into line 42 as shown in FIG. 2). For example, such control may be implemented as a function of one or more signals from the infusion apparatus 12 (e.g., signals provided by the force sensor 60 and a displacement sensor of the actuator 50 shown in FIG. 2).

The controller 14 operatively coupled to the infusion apparatus 12 may be any hardware/software architecture configured to provide the desired functionality. For example, the controller may include circuitry for sampling the force sensor, processing apparatus and associated software for processing data (e.g., signals representative of force or pressure measurements to implement the monitoring, detection, and/or pressure priming algorithms described herein), output circuitry to generate control signals for use in controlling infusion fluid flow rates, commanding delivery of one or more boluses, accelerating delivery of one or more commands and/or one or more boluses, changing and/or accelerating the rate of the delivery of boluses, controlling one or more alarms, etc. As described herein with reference to FIG. 3, for example, such controller functionality may be carried out by the apparatus 360 described therein.

Such processing apparatus may be, for example, any fixed or mobile computer system (e.g., a personal computer or mini-computer associated with, for example, a fluid treatment or processing system, such as a dialysis system). The exact configuration of the computing apparatus is not limiting and essentially any device capable of providing suitable computing capabilities and control capabilities (e.g., control of the infusion apparatus 12, monitoring of the force sensor signals to determine if the infusion line appears occluded, control delivery of commands to the actuator for delivery of one or more boluses, etc.) may be used. Further, various peripheral devices, such as a computer display, mouse, keyboard, memory, printer, scanner, are contemplated to be used in combination with processing apparatus, and its associated data storage. For example, data storage may allow for access to processing programs or routines and one or more other types of data that may be employed to carry out the illustrative methods and functionality as described herein.

In one or more embodiments, the methods or systems described herein may be implemented using one or more computer programs or processes (or systems including such processes or programs) executed on programmable computers, such as computers that include, for example, processing capabilities, data storage (e.g., volatile or non-volatile memory and/or storage elements), input devices, and output devices. For example, the systems and methods described herein may be considered to include multiple processes or programs that may be implemented alone or in combination. Program code and/or logic described herein may be applied to input data to perform functionality described herein and generate desired output information. The output information may be applied as input to one or more other devices and/or processes as described herein or as would be applied in a known fashion. For example, processing programs or routines may include programs or routines for performing various algorithms, including standardization algorithms, comparison algorithms, or any other processing required to implement one or more embodiments described herein, such as those for performing analysis of measurement data, generation of control signals, etc.

Software or programs used to implement the functionality described herein may be provided using any programmable language, e.g., a high level procedural and/or object orientated programming language that is suitable for communicating with a processing apparatus. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the methods and systems described herein may be implemented using a computer readable storage medium, configured with a computer program, where the storage medium so configured causes the processing apparatus to operate in a specific and predefined manner to perform functions described herein.

Further, for example, the infusion system 10 may be used in any fluid processing systems that would benefit therefrom. For example, exemplary systems that may benefit from such pressure priming algorithms may include systems, generally referred to as dialysis systems. The general term dialysis as used herein includes hemodialysis, hemofiltration, hemodiafiltration, and therapeutic plasma exchange (TPE), among other similar treatment procedures. In dialysis generally, blood is taken out of the body and exposed to a treatment device to separate substances therefrom and/or to add substances thereto, and is then returned to the body. Although an extracorporeal blood treatment system 310 capable of performing general dialysis (as defined above, including TPE) is described herein with reference to FIG. 3, other systems such as those for infusion of drugs, performance of continuous renal replacement therapy (CRRT), extracorporeal membrane oxygenation (ECMO), hemoperfusion (HP), molecular adsorbent recirculating systems (MARS), cascade, etc. may benefit from the systems, methods, and apparatus described herein and the present disclosure is not limited to the specific fluid processing or delivery systems described herein.

In the perspective view of FIG. 3, the exemplary extracorporeal blood treatment system 310, which may implement a fluid delivery system 10 including pressure priming functionality as described generally with reference to FIG. 1, may include a blood circuit 312 having first and second tubing segments 314 and 316 which are both connected to the vascular system of a patient 318 via access and return devices 317 and 319, respectively. Devices 317 and 319 may be cannulas, catheters, winged needles or the like as would be understood by one skilled in the art. Tubing segments 314 and 316 are also connected to a filtration or processing unit 320. In dialysis, filtration unit 320 is a dialyzer, which is also often referred to as a filter. In TPE, it may also be referred to as a plasma filter. In this exemplary system 310, a peristaltic pump 324 is disposed in operative association with the first tubing segment 314. Numerous other component devices of blood circuit 312 are also included, such as, for example, pressure sensors, tube clamps, etc.

Also shown in FIG. 3 is the processing fluid or filtrate side of system 310 which generally includes a processing fluid circuit 340 having first and second processing fluid tubing segments 341 and 342. Each of these tubing segments is connected to the filtration unit 320. In FIG. 3, a respective fluid pump 344, 346 is operatively associated with each of these tubing segments 341 and 342. First tubing segment 341 is also connected to a processing fluid source (e.g., fluid bag 349) which may include electrolytes pre-mixed therein. Second tubing segment 342 is connected to a waste collection device (e.g., a waste container such as a bag 353). A pressure sensor 354 may be disposed in second dialysis fluid tubing segment 342.

FIG. 3 shows a system which is common as a basic model for numerous dialysis procedures. Additional fluid lines, circuits, and components may be added (or deleted) to increase treatment options. Further, as shown in FIG. 3, the system 310 includes an extracorporeal blood dialysis control apparatus 360 which provides numerous treatment options which are controlled and/or monitored via the control/display screen 361 (e.g., a control apparatus or controller provided in a system housing 393). Touch-screen controls may be incorporated herewith and/or other conventional knobs or buttons (not shown) may be used; e.g., as part of a graphical user interface. Other and more detailed information regarding an example apparatus 360 may be found in U.S. Pat. Nos. 5,679,245; 5,762,805; 5,776,345; and 5,910,252; inter alia.

In other words, at least in one embodiment, the system 310 shows an extracorporeal blood circuit 312, provided with an arterial line or access line and a return line, as well as a circuit 340 for circulation of various treatment fluids that may include, according to the selected treatment, for example, a line supplying a dialysis fluid to the filter 320 and a discharge line for a used fluid exiting from the filter 320. Further, the system 310 includes one or more infusion lines for various medical liquids (e.g., substitution liquids, anticoagulants such as heparin, fluids for use in combination with other anticoagulants such as for citrate anticoagulation, etc.). For example, an infusion apparatus 362 including a syringe 364 (e.g., such as described herein or any other infusion apparatus) may be used to deliver anticoagulant through an anticoagulant line 365 to the extracorporeal blood circuit 312 (e.g., a one way valve may be used in the fluid connection of the infusion apparatus to the blood circuit). For example, the infusion apparatus may be suitable for administering liquids at low flow-rates.

A general dialysis treatment procedure, as performed, for example, with an apparatus described with reference to FIG. 3, will be generally described for exemplary purposes only. First, blood is removed from the patient 318 via access device 317 and flows through access line 314 to the filter 320. To reduce the risk of coagulation of the extracorporeal blood, infusion of an anticoagulant (e.g., heparin) into the extracorporeal blood circuit 312 is provided by infusion apparatus 362, 364 (e.g., generally into the arterial line, through an infusion line, for example, line 365, with relatively low infusion flow rates). If citrate anticoagulation is used (e.g., a bagged citrate laden solution being delivered to the access line 314 pre-filter using a pre-blood pump infusion process), then infusion apparatus 362, 364 (e.g., syringe pump) may be used to provide calcium replacement via an infusion line connected to the return line or connected directly to the patient. Filter 320 processes this blood according to a selected one or more of a number of extracorporeal blood treatment protocols (e.g., selected and controlled via screen interface 361 of control apparatus 360; which may provide a graphical user interface) and then the processed or treated blood is returned to the patient 318 through return line 316 and return device 319 inserted in or otherwise connected to the vascular system of the patient 318. The blood flow path to and from the patient 318, which includes the access device 317, the access line 314, the filter 320, as well as the return line 316 and return device 319 back to the patient, forms the extracorporeal blood flow circuit 312.

Pressure sensors may be used to sense various pressures in the system 310. For example, the pressure sensor 327 (e.g., an access pressure pod apparatus such as described in WO2014/099779 entitled "Blood Set Component Connection Detection") may be connected in the access line 314 and allow the fluid pressure in the access line 314 to be monitored and the second pressure sensor 328 (e.g., including a filter pressure pod apparatus) may be connected in the blood circuit 312 between the first pump 324 and the blood entrance into the filter 320 and may be used to detect and monitor the pressure of the blood supplied to the entrance of the filter 320.

The system 310 may further include a deaeration chamber 325 in the return line to provide a conveyance path that operates like a vortex to propel air out of the blood. Post-filter replacement solution may be added into the deaeration chamber on the top of the blood to prevent an air/blood interface. A deaeration chamber monitor line connects the deaeration chamber 325 to an internal pressure transducer within the system housing 393 using a connection apparatus, such as, for example, a return pressure port 329. This enables return pressure monitoring, and removal of air from the deaeration chamber, if needed. A return clamp 331 connected in the blood circuit 312 selectively allows or terminates the flow of blood through the blood circuit 312 (e.g., return clamp 331 may be activated whenever air is detected in the blood by bubble detector 326). Further, pump 366 may deliver replacement fluid from a replacement fluid container or bag 368 through a replacement fluid line 370.

The filtration unit 320, the flow tubing lines, and the other components in the primary and secondary flow circuits 312 and 340 described herein (with the exception, for example, of the pumps and perhaps a few other items) may be formed as an integral, replaceable unit (e.g., an extracorporeal blood set). An example of such an integral replaceable unit is described in greater detail in U.S. Pat. No. 5,441,636 entitled Integrated Blood Treatment Fluid Module (see also, U.S. Pat. No. 5,679,245, entitled Retention Device for Extracorporeal Treatment Apparatus).

Measurements by the pressure sensors 327, 328 and 354, as well as the return line pressure sensor connected to the deaeration chamber monitor line 391 may be used for one or more various control functions (e.g., used by the apparatus 360 in internal monitoring to make internal decisions and/or automatic adjustments to modify fluid flow parameters, such as pressure priming as described herein). One skilled in the art will recognize that such pressure measurements may be obtained in any known manner using pressure sensors or portions thereof integrated with the extracorporeal blood set or pressure sensors separate therefrom operable to sense pressures at various positions of the system to provide measurements suitable to carry out functionality described herein. For example, one or more of the pressure sensors 327, 328, and 354 may be provided with use of a pressure pod apparatus of a diaphragm type.

The infusion apparatus 362 (including a replaceable fluid dispenser or syringe 364) may include a force sensor 18 (e.g., as schematically shown in FIG. 1) to provide a force signal associated therewith. For example, the force sensor may be a load cell configured to provide an electrical signal which is sent to a controller, such as controller 14 shown in FIG. 1 (e.g., an electrical micro-processing unit in control apparatus 360 for analysis of the signals for use in determining whether the infusion line 365 looks occluded) which may then process the signal for display, storage or use by software (or hardware) for calculations, or for carrying out any other functionality (e.g., to determine whether pressure priming is to be performed, to determine the need initiate an alarm, etc.). The same or different controller or processing unit of apparatus 360 may be used for processing signals from other components of the system 310 to control a treatment being provided.

The systems and apparatus described with reference to FIGS. 1-3 are configured to determine the need for pressure priming of a replacement fluid dispenser (e.g., syringe 364 in FIG. 3) when such a replacement fluid dispenser is coupled to an actuator apparatus (e.g., actuator or pump mechanism) to replace a prior, for example, empty or nonfunctional fluid dispenser connected in the infusion apparatus (e.g., infusion apparatus 12 as shown in FIG. 1, the infusion apparatus 36 as shown in FIG. 2, and infusion apparatus 362 with syringe 364 as shown in FIG. 3). For example, a controller thereof, as described herein, is configured to acquire from a force sensor thereof, a signal which is indicative of a resistant force (e.g., which is effectively opposed to the pushing structure 58 advancement as shown and described with reference to FIG. 2) representative of the pressure of the fluid being infused. For example, this force signal, one or more actuator signals (e.g., representative of actuator displacement), and/or one or more pressure signals obtained by the controller may be used to determine the need for pressure priming of a replacement fluid dispenser (e.g., determine one or more metrics indicative of the need for pressure priming, comparing one or more measurable pressures to syringe pressure to determine the need for pressure priming, comparing calculated volumes based on actuator displacement to syringe volumes to determine the need for pressure priming, etc.). The resistant force may be a function of many parameters depending on the configuration of the system, among which include the pressure of the fluid internally of the syringe, the cylinder section the plunger runs through, the type of syringe, the speed of advancement of the plunger, etc.

One or more pressure priming algorithms may use different input parameters to determine the need for pressure priming depending upon the connection of the infusion line (e.g., line 365 in FIG. 3) in the system. For example, different pressures may be used in the process for determining the need for pressure priming depending upon whether the infusion line is connected pre-filter (e.g., delivery of heparin), connected post-filter (e.g., delivery of replacement calcium) to the return line, or connected post-filter (e.g., delivery of replacement calcium) directly to the patient.

Figure 4:
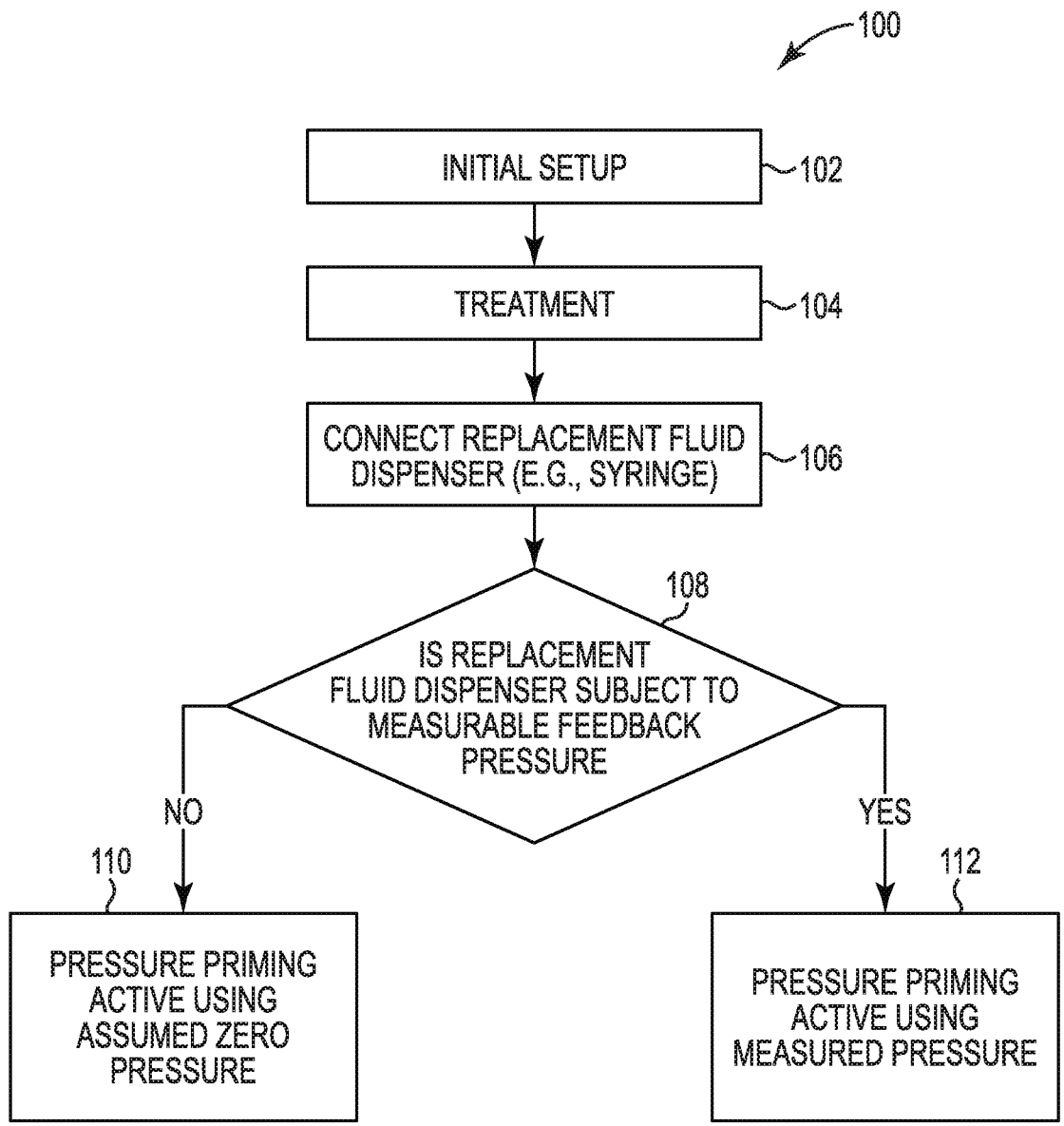
FIG. 4 is a block diagram illustrating an exemplary algorithm for use in pressure priming of an infusion apparatus for delivery of a fluid which may be implemented by a system, for example, such as shown generally in FIG. 3.
Figure 11:
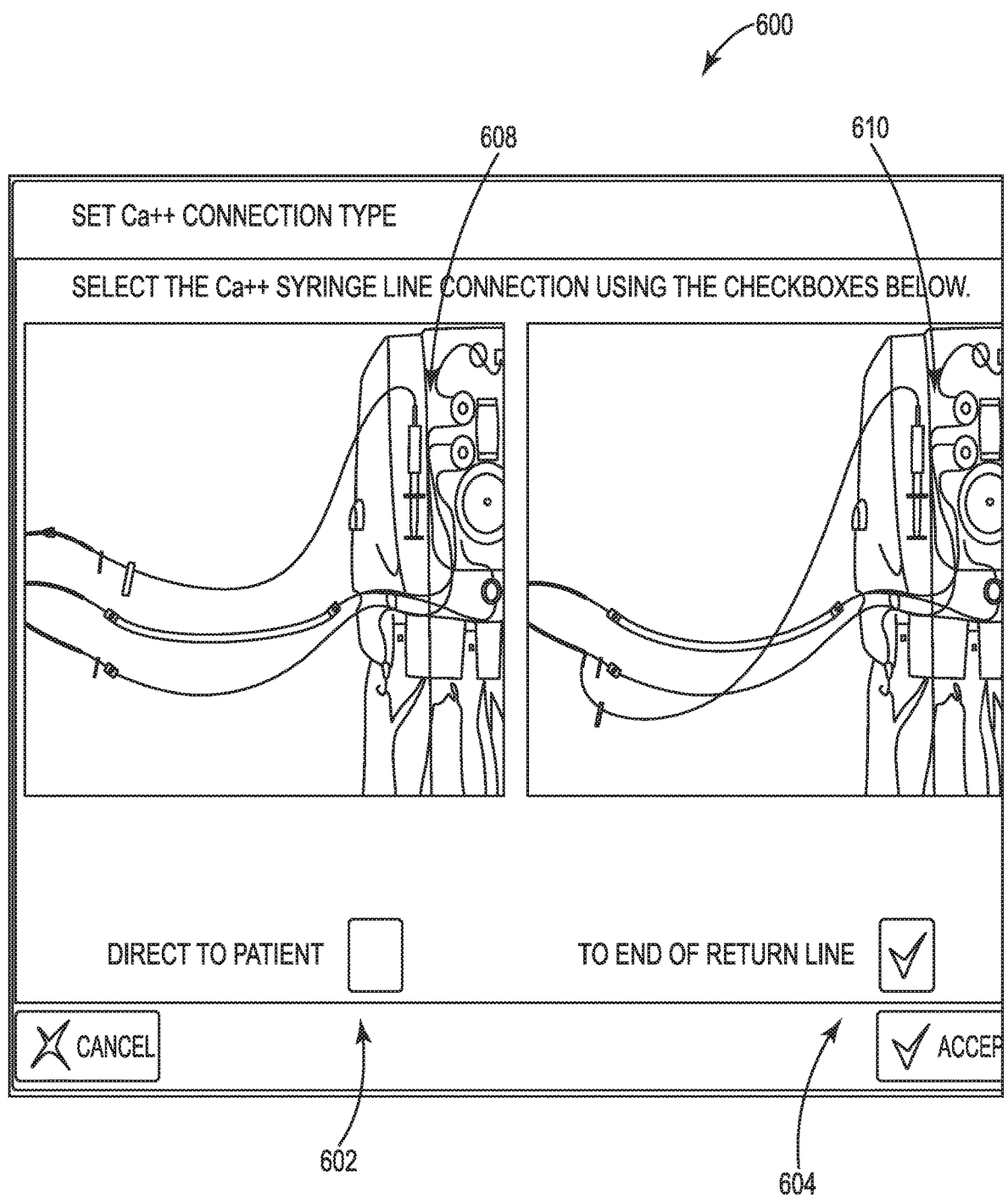
FIG. 11 is a graphical user interface illustration for use in illustrating an exemplary algorithm for use in pressure priming of an infusion apparatus, such as may be implemented by a system, for example, as shown generally in FIG. 3.

FIG. 4 provides a block diagram of a method 100 for use in determining, for example, one or more input parameters (e.g., feedback pressures) to be used for determining the need for pressure priming. For example, at initial set up 102 the user is presented with an interface for providing treatment parameter inputs to the system during setup. One exemplary interface 600 is shown in FIG. 11; however, such information may be input by a user in any other suitable manner (e.g., pulldown menus, text entry, etc.). As shown in FIG. 11, the interface 600 includes regions graphically depicting the connection of the infusion line for providing replacement calcium either directly to the patient (region 608) or to the return line (region 610). Further, the user is directed to select which connection is being made by the user by checking the box in either region 602 (Direct to Patient) or region 604 (To end of Return Line). One will recognize that another graphical interface may be provided to the user for selection of whether a heparin anticoagulant is being used or whether a citrate anticoagulant is being used. Thereafter, if citrate anticoagulation is being used, then FIG. 11 may be displayed.

Depending upon the user's selection during the initial setup 102, different pressures may be used for determining the need for pressure priming. For example, if the connection chosen by the user is a heparin anticoagulant connection (e.g., infusion line connected pre-filter) then a pressure measurement at the input of the filter of the treatment system (e.g., filter 320 of system 310 of FIG. 3) may be made by a suitable pressure sensor (e.g., sensor 327 of FIG. 3) and used for determining the need for pressure priming. However, for example, if the connection chosen by the user is a citrate-based connection, and if the user has selected the connection of the infusion line for providing replacement calcium to the return line (e.g., region 604 in FIG. 11), then pressure measurement in the return line of the treatment system (e.g., system 310 of FIG. 3) may be made by a suitable pressure sensor (e.g., transducer connected to port 329 of FIG. 3) and used for determining the need for pressure priming. Yet, still further, for example, if the connection chosen by the user is a citrate-based connection, and if the user has selected the connection of the infusion line for providing replacement calcium directly to the patient (e.g., region 602 in FIG. 11), then a predetermined pressure (e.g., a zero pressure) may be set and used for determining the need for pressure priming.

As such, and with further reference to FIG. 4, after initial setup 102 and after initiating treatment 104, a replaceable fluid dispenser being used during treatment 104 may need to be replaced (e.g., the dispenser may be empty, the dispenser may become nonfunctional, etc.). A replacement fluid dispenser (e.g., a refilled syringe or a new replacement syringe) may then be connected in the infusion apparatus (block 106). To determine what parameters are to be used in determining pressure priming, the system looks to the selected connection inputted by the user (e.g., such as with the graphical user interface shown in FIG. 11). As shown in decision block 108, if the replacement fluid dispenser is subject to a measurable feedback pressure (e.g., a measurable feedback pressure at the input of the filter determinable by the user's selection of a heparin connection or a measurable feedback pressure of the return line determinable by a user's selection of the calcium replacement connection to the return line), then pressure priming is active in the system and uses the measurable feedback pressure as an input to determine to what extent pressure priming is allowed (block 112). Likewise, if the replacement fluid dispenser is not subject to a measurable feedback pressure (e.g., determinable by the user's selection of a calcium replacement connection directly to the patient), then pressure priming is active in the system and uses the predetermined pressure (e.g., a zero pressure) as an input to determine to what extent pressure priming is allowed (block 110).

In other words, the controller of the blood treatment system uses the information provided by the user via the user interface to determine to what extent pressure priming is allowed. For example, when citrate anticoagulation is being used, at least in one embodiment, the controller is configured to determine, upon connection of a replacement fluid dispenser in the infusion apparatus and if the user provided a selected connection of the infusion line to the return blood line, whether a system back pressure based on a measurable pressure of the return blood line is preventing the infusion apparatus from delivering one or more boluses thereto. If it is determined that such boluses are being prevented from delivery to the return blood line, then the replacement fluid dispenser may be pressure primed. Likewise, the controller is configured to determine, upon connection of a replacement fluid dispenser in the infusion apparatus and if the user provided a selected connection of the infusion line directly to the patient, whether a frictional force associated with the fluid dispenser (e.g., based on the stiffness of the syringe) is preventing the infusion apparatus from delivering one or more boluses into the patient. Rather, the controller uses a predetermined pressure in making a determination as to what extent pressure priming is allowed (e.g., a zero pressure).

Figure 5:
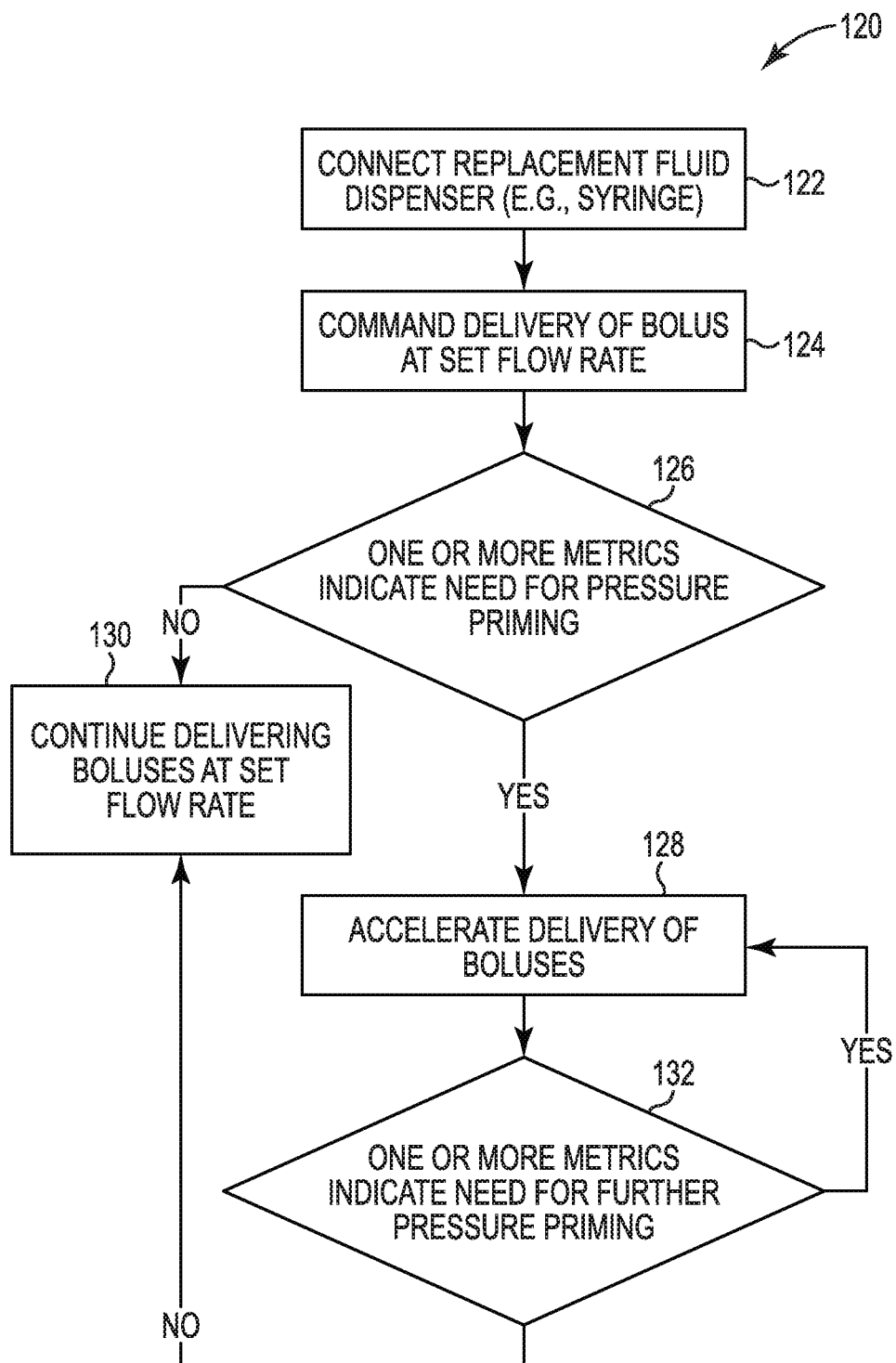

One exemplary pressure priming algorithm 120 to determine whether to pressure prime a replacement fluid dispenser (e.g., a syringe) and then to perform such pressure priming is shown in the block diagram of FIG. 5. For example, upon connection of a replacement fluid dispenser into an infusion apparatus (block 122) such as described herein, the controller of the system commands the infusion apparatus to deliver a bolus into the infusion line at a set flow rate (block 124). For example, the set flow rate may be the flow rate as set by a user for delivery of fluid by the infusion apparatus (e.g., via a treatment prescription, or an adjusted of a treatment parameter during treatment). Generally, for the delivery of anticoagulant (e.g., heparin) or fluids associated with an anticoagulant (e.g., calcium replacement), the set flow rate is generally a low flow rate. For example, such a low flow rate may be a flow rate that is less 3.91 mL per hour, less than 3.0 ml per hour, less than 2.0 ml per hour, less than 1.5 ml per hour, less than 1.0 ml per hour, or less than 0.5 ml per hour. The lower the set flow rate, the more beneficial pressure priming becomes as will become clear from the description herein.

Such set flow rates are associated with time intervals between commands to the infusion apparatus for delivery of boluses. For example, at a set flow rate of 0.5 ml per hour, the time interval between the commands for the delivery of boluses is about 360 seconds. In other words, to deliver 0.5 mL per hour, the infusion apparatus is commanded every 360 seconds such that the actuator thereof delivers a bolus of fluid when commanded. The longer the time interval between commanded boluses of a set flow rate, the more beneficial pressure priming becomes as will become clear from the description herein. For example, pressure priming is beneficial where the time interval between commands provided to deliver boluses at the set flow rate is greater than 45 seconds, or where the time interval between commands provided to deliver boluses at the set flow rate is 90 seconds or greater, or where the time interval between commands provided to deliver boluses at the set flow rate is 180 seconds or greater, or where the time interval between commands provided to deliver boluses at the set flow rate is 360 seconds or greater.

After commanding the infusion apparatus to deliver a bolus into the infusion line at the set flow rate (block 124), one or more metrics are used to determine whether there is a need for pressure priming (block 126). For example, such metrics may include or be based on any parameters indicative of whether a system back pressure operating on the replacement fluid dispenser is preventing the infusion apparatus when commanded from delivering the bolus into the infusion line, whether a frictional force associated with the fluid dispenser is preventing the infusion apparatus from delivering one or more boluses, etc. As such, various metrics may include feedback pressures (e.g., pressures taken at the inlet of the filter, pressures of the return line, etc.) that can be compared to syringe pressures, the set flow rate itself (e.g., the time interval between commands to deliver boluses at the set flow rate), measurements of displacement of an actuator of the infusion apparatus used to calculate volumes comparable to syringe volumes, metrics indicative of whether the infusion line looks occluded (e.g., using a force signal from the force sensor of the infusion apparatus), etc.

If the one or more metrics do not indicate a need for pressure priming (e.g., boluses are indicated as being successfully delivered to one of the access blood line, the return blood line, and the patient) (block 126), then commands to the infusion apparatus to deliver boluses into the infusion line at the set flow rate are continued (block 130). However, if the one or more metrics indicate a need for pressure priming (e.g., a system back pressure operating on the replacement fluid dispenser is preventing the infusion apparatus when commanded from delivering one or more boluses into the blood circuit, a frictional force associated with the fluid dispenser is preventing the infusion apparatus from delivering one or more boluses into the patient, etc.) (block 126), then the pressure in the replacement fluid dispenser is pressure primed (i.e., increased) by accelerating one or more commands to the infusion apparatus to deliver one or more boluses into the infusion line. By accelerating the one or more commands to the infusion apparatus to deliver one or more boluses into the infusion line, a time required to overcome, for example, the system back pressure or frictional forces preventing delivery of the boluses to one of the access blood line, the return blood line, and the patient is decreased. In other words, if commands to deliver boluses to the infusion system were not accelerated, then such commands would continue to be provided at the set flow rate. Since the set flow rate is a relatively low flow rate, it may take a substantial time period at such a low flow rate for the pressure in the fluid dispenser to increase and overcome, for example, the system back pressure or frictional forces operating on the fluid dispenser. By accelerating such commands to the infusion apparatus at a rate that is higher than the set flow rate, such a time period is decreased. For example, the time interval between an accelerated command and a prior command immediately preceding the accelerated command would be less than a time interval between commands provided to deliver boluses at the set flow rate.

It will be recognized that the pressure priming algorithm 120 may operate to accelerate one or more commands to deliver boluses (block 128) in various manners. For example, the controller may provide for accelerating commands by commanding the infusion apparatus to operate at an accelerated flow rate higher than the set flow rate, may provide for accelerating one or more commands by determining on a command by command basis whether the next command to the infusion apparatus to deliver a bolus is to be accelerated or not accelerated, may provide a group of accelerated commands depending upon one or more parameters (e.g., pressure level of syringe indicates a certain number of commands may be accelerated), etc.

With further reference to FIG. 5, after one or more accelerated commands have been made to the infusion apparatus, it is then determined whether one or more metrics indicate need for further pressure priming (block 132). Such a determination may be similar to that provided in decision block 126. If it is determined that there is a need for further pressure priming, one or more commands to the infusion apparatus to attempt to deliver boluses to one of the access blood line, the return blood line, and the patient are again accelerated (block 128). If it is determined that there is not a need for further pressure priming, then the commands to the infusion apparatus are provided at the set flow rate (block 130). As further described herein, such acceleration of commands may, for example, terminate based upon the successful delivery of a predetermined number of boluses to one of the access blood line, the return blood line, and the patient, for example, as indicated by one or more metrics (block 132).

Figure 6:
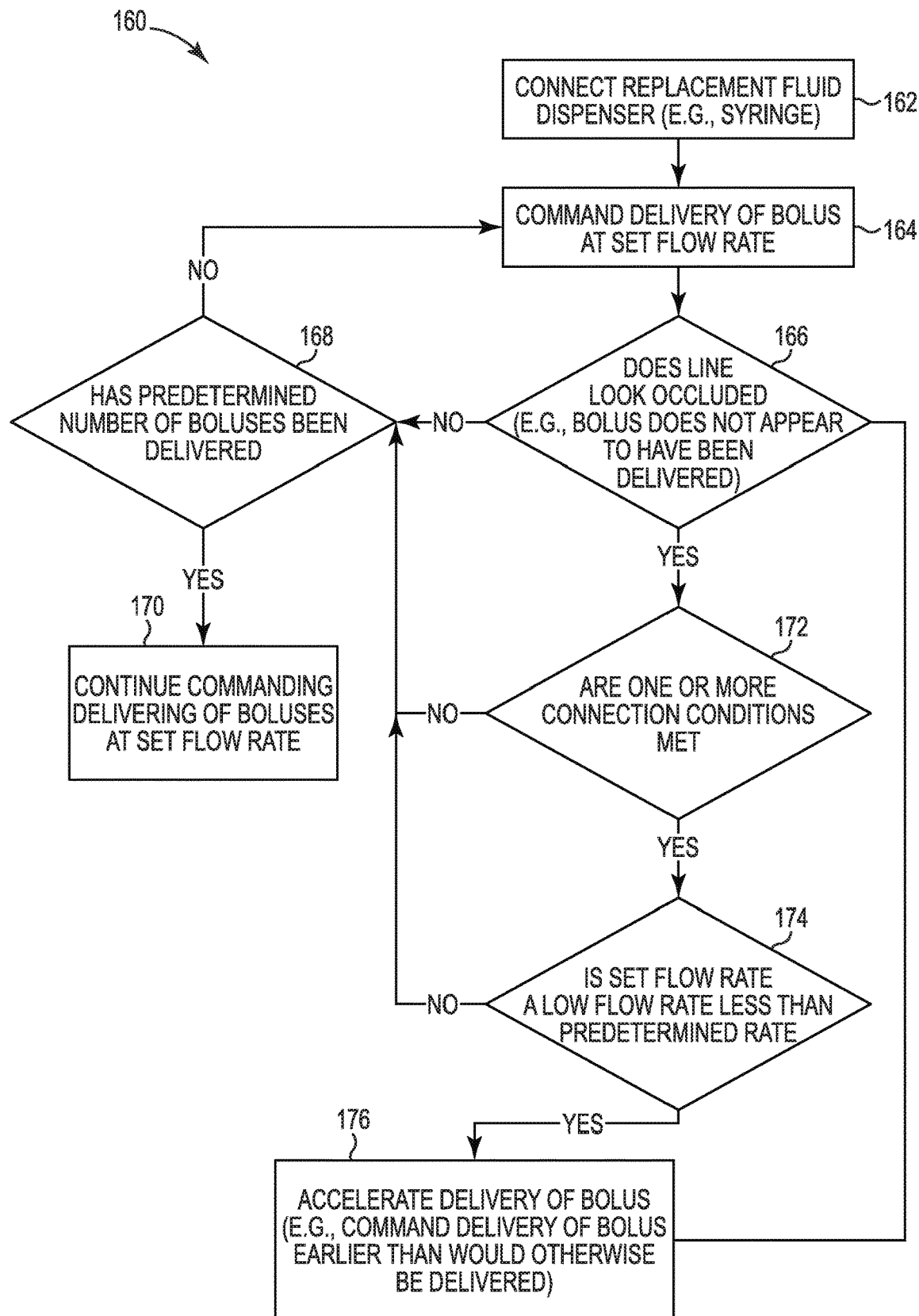
FIG. 6 is a block diagram illustrating another more detailed exemplary algorithm for use in pressure priming of an infusion apparatus for delivery of a fluid which may be implemented by a system, for example, such as shown generally in FIG. 3.

Another exemplary pressure priming algorithm 160 to determine whether to pressure prime a replacement fluid dispenser (e.g., a syringe) and then to perform such pressure priming is shown in the block diagram of FIG. 6. This block diagram shows a more detailed embodiment of one or more processes more generally described in FIG. 5. For example, upon connection of a replacement fluid dispenser into an infusion apparatus (block 162) such as described herein, the controller of the system commands infusion apparatus to deliver a bolus into the infusion line at a set flow rate (block 164). For example, the set flow rate may be the low flow rate as set by a user for delivery of fluid by the infusion apparatus (e.g., via a treatment prescription) as described with reference to FIG. 5.

After commanding the infusion apparatus to deliver a bolus into the infusion line at the set flow rate (block 164), one or more metrics are used to determine whether there is a need for pressure priming (e.g., whether the system back pressure operating on the replacement fluid dispenser or frictional forces associated with the syringe has prevented the infusion apparatus from delivering one or more boluses to one of the access blood line, the return blood line, and the patient when the infusion apparatus is commanded to do so). For example, in one embodiment, it may be determined whether the infusion line looks occluded (block 166). In other words, for example, it is determined whether the bolus has or has not been successfully delivered into the infusion line. Many occlusion detection techniques are available for determining whether a bolus has been successfully delivered. The present disclosure is not limited to any particular technique for determining whether the infusion line looks occluded, although some techniques as described herein may be more beneficial for one reason or another or provide better results than others.

The determination of whether the infusion line looks occluded (block 166) may be based on the measurable force response over time. For example, each bolus of the fluid being infused on a bolus by bolus basis may be represented or correspond to a force measurement associated with the infusion apparatus used to provide each bolus. For example, as previously described herein, with respect to FIG. 1, the infusion apparatus 12 is associated with a force sensor 18 configured to provide a force signal to controller 14 representative of the fluid flow being delivered by infusion apparatus 12. As described, each bolus of the fluid flow may result in a measurable force response (e.g., measurable over time by force sensor 18).

For example, in operation, after a command is provided to the infusion apparatus to deliver a bolus (e.g., for example, after a push force has been provided by the actuator of the infusion apparatus), the force measured by the sensor 18 of FIG. 1, may be used to generate a metric indicative of whether the infusion line looks occluded. If an appearance of occlusion is present, then a bolus is likely being prevented from delivery into the infusion line by the system back pressure.

For example, a command to the infusion apparatus to deliver a bolus into the infusion line results in a measurable force response. Generally, in normal operation, when a bolus has been successfully delivered to one of the access blood line, the return blood line, and the patient, the measurable force response includes a maximum force reached shortly after the command followed by a rate of decay in the force response back to an equilibrium value (see, e.g., FIG. 10). In abnormal infusion operation (e.g., when a partial or total occlusion exists in the fluid flow), or when a system back pressure operating on the replacement fluid dispenser prevents delivery of a bolus to one of the access blood line, the return blood line, and the patient, a maximum force will also be reached shortly after the command, however, the rate of decay of the force response back to an equilibrium value will be different than in normal operation (e.g., the rate of decay may be much slower or even non-existent in the cases of a complete occlusion, or when a system back pressure prevents the bolus from being delivered). The differences in the force response for normal versus abnormal operation can be used as described herein to provide one or more metrics for determining whether the infusion apparatus has been prevented from delivering a bolus to one of the access blood line, the return blood line, and the patient when commanded.

For example, in one or more embodiments (various other embodiments also being possible), by integrating the force signal representative of the force response for a corresponding commanded bolus, a value may be obtained related to the maximum force and the rate of decay of the force. By dividing this integrated value by another value related to the maximum force (e.g., a normalizing value), a ratio (e.g., an area ratio) that is related substantially only to the rate of decay of the force associated with the commanded bolus can be obtained. Since the ratio related substantially only to the rate of decay of the force is directly related to the resistance of flow from the infusion apparatus, the ratio provides an indicator of whether the infusion line appears to be occluded (i.e., which is indicative of the infusion apparatus being prevented from delivering a bolus to one of the access blood line, the return blood line, and the patient when commanded).

Figure 10:
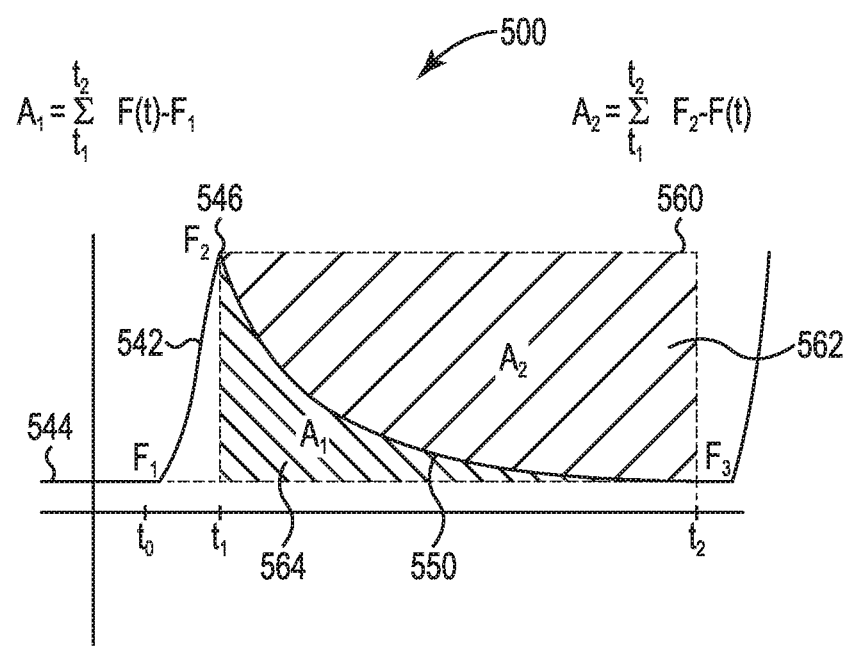
FIG. 10 is a graphical illustration of an exemplary force response for use in describing the exemplary algorithms for pressure priming of an infusion apparatus.

For example, with further reference to the measurable force response graphically illustrated in FIG. 10, for a normal and successful delivery of a bolus to one of the access blood line, the return blood line, and the patient by the infusion apparatus when commanded, the measurable force response generally starts at time $t_0$, where the commanding of the actuator provides for a rapid increase in the force sensed (e.g., over and above the equilibrium force F1). This is shown by graph line 542 from time t0 to time t1 where a maximum force F2 is reached shortly after the command to deliver a bolus (e.g., the actuator applies a force sensed by the sensor 18). Further, as shown in FIG. 10, after the maximum force F2 is reached, a rate of decay in the force response back to an equilibrium force F3 occurs as shown by graph line 550 in FIG. 10 during the period from time t1 to time t2.

When, for example, the system back pressure is preventing the commanded bolus from being delivered (e.g., the infusion line appears to be occluded), a maximum force F2 will also be reached shortly after the command to the infusion apparatus is issued. However, the rate of decay of the force response back to equilibrium will be different. For example, when the commanded bolus is prevented from being delivered, the rate of decay may be virtually nonexistent such that following the reaching of the maximum force F2 at time t1, the force response will be substantially maintained at force F2 generally coinciding with graph line 560. The differences in the force response between when the commanded bolus is prevented from being delivered and when a commanded bolus is delivered successfully can be used as described herein to determine if the occlusion line looks occluded and whether pressure priming should be performed.

For example, as shown in FIG. 10, one can refer to the area 564 under the force response F(t) (e.g., representative of the additional force over equilibrium due to the perturbation) as A1. The area 562 above the force response may be referred to as A2 (e.g., representative of the force response relative to the maximum force F2). In other words, $A_1 = \Sigma_{t1}{'}2 F(t) - F_1$, and $A_2 = \Sigma_{t1}{'}2 F_2 - F(t)$.

An integrated force response value may be determined for a corresponding commanded bolus in the fluid flow using integration of the force signal over a time period (e.g., summation over a time period). A ratio between the integrated force response value and a normalizing value may also be provided. As further described herein, the integrated force response value and the normalizing value may take either the numerator or denominator position of such a ratio. The normalizing value determined for inclusion in the ratio may be based on the maximum force (e.g., the maximum force 546 shown in FIG. 10). Various normalizing values based on the maximum force may be used. For example, the normalizing value determined for a corresponding commanded bolus may be representative of an integration, taken over the accumulation time, of the maximum force relative to equilibrium force. For example, the area A1 plus area A2 (i.e., A1+A2) as shown in FIG. 10 may be a normalizing value determined for a corresponding commanded bolus. Further, for example, the normalizing value determined for a corresponding commanded bolus may be representative of an integration, taken over the accumulation time, of the maximum force relative to the force response (e.g., the integration being initiated at the occurrence of the maximum force, such as, for example, at time t1 as shown in FIG. 10, and the extending through the accumulation time period ending at time t2). For example, the area A2 as shown in FIG. 10 may be a normalizing value determined for a corresponding bolus.

Such various ratios between the integrated force response value and a normalizing value (which ratios may be used for determining whether a bolus is prevented from being delivered to one of the access blood line, the return blood line, and the patient upon command) may be described using the graphically illustrated areas shown in FIG. 10 for a measurable force response. For example, such ratios based on areas associated with the force response may include:

$A1/A2$ or $A2/A1$;

$A1/(A1+A2)$ or $(A1+A2)/A1$; or $A2/(A1+A2)$ or $(A1+A2)/A2$.

Further, for example, threshold ratios can be used, e.g., for comparison to ratios determined for a particular commanded bolus to determine if the commanded bolus was successfully delivered or whether, for example, the back pressure and/or frictional forces of the system prevented the bolus from being delivered successfully. For example, a threshold ratio that would indicate the infusion line looks occluded using A1/A2 may be 2.0; whereas, a threshold ratio indicative of an occlusion associated with A1/(A1+A2) may be 0.2. Area ratios, as well as thresholds related thereto, used for determining whether a line is occluded are described, for example, in WO2014/105606 entitled "Occlusion Detection in Delivery of Fluids" which is incorporated herein by reference.

One skilled in the art will recognize that various values for inclusion in the ratio may be determined (e.g., calculated) in various ways. Such calculations may include integrations and/or summations which directly result in such values, but other calculations may involve the use of integrated values in indirect manners. For example, the integrated force response value may be determined by integrating the force signal over a time period (e.g., summation over time) (e.g., integrating the force signal over the time period t1 to t2 as shown in FIG. 10 resulting in A1), while the integrated force response value, equivalent, for example, to area A2 may be calculated by providing the integration value representative of area A1 and, subtracting such area from an area equivalent to area (A1+A2) (e.g., (A1+A2) being calculable from (F2−F1) accumulated over time t1 to t2). Further, for example, the normalizing value equivalent to area A1 plus area A2 (i.e., A1+A2) may be determined from (F2−F1) being accumulated over time t1 to t2, while the normalizing value equivalent to area A2 may be calculated in the same manner as it may be calculated when used as an integrated force response value.

In one or more embodiments described herein, various parameters may be adjusted to optimize the implementation of the functionality to determine whether the line looks occluded or not. For example, the amount of time to integrate may be adjustable, the ratios used as thresholds which indicate an occlusion or abnormal condition (e.g., the magnitude of such ratios) may be adjustable, etc. Such adjustability can be used to accommodate a wide range of infusion device compliances, resistances and inconsistencies. Further, because the ratio used is a normalized quantity, it is relatively independent of infusion device and replacement fluid dispenser characteristics; which greatly simplifies the determination of such parameters suitable to provide effective occlusion detection.

Figure 9:
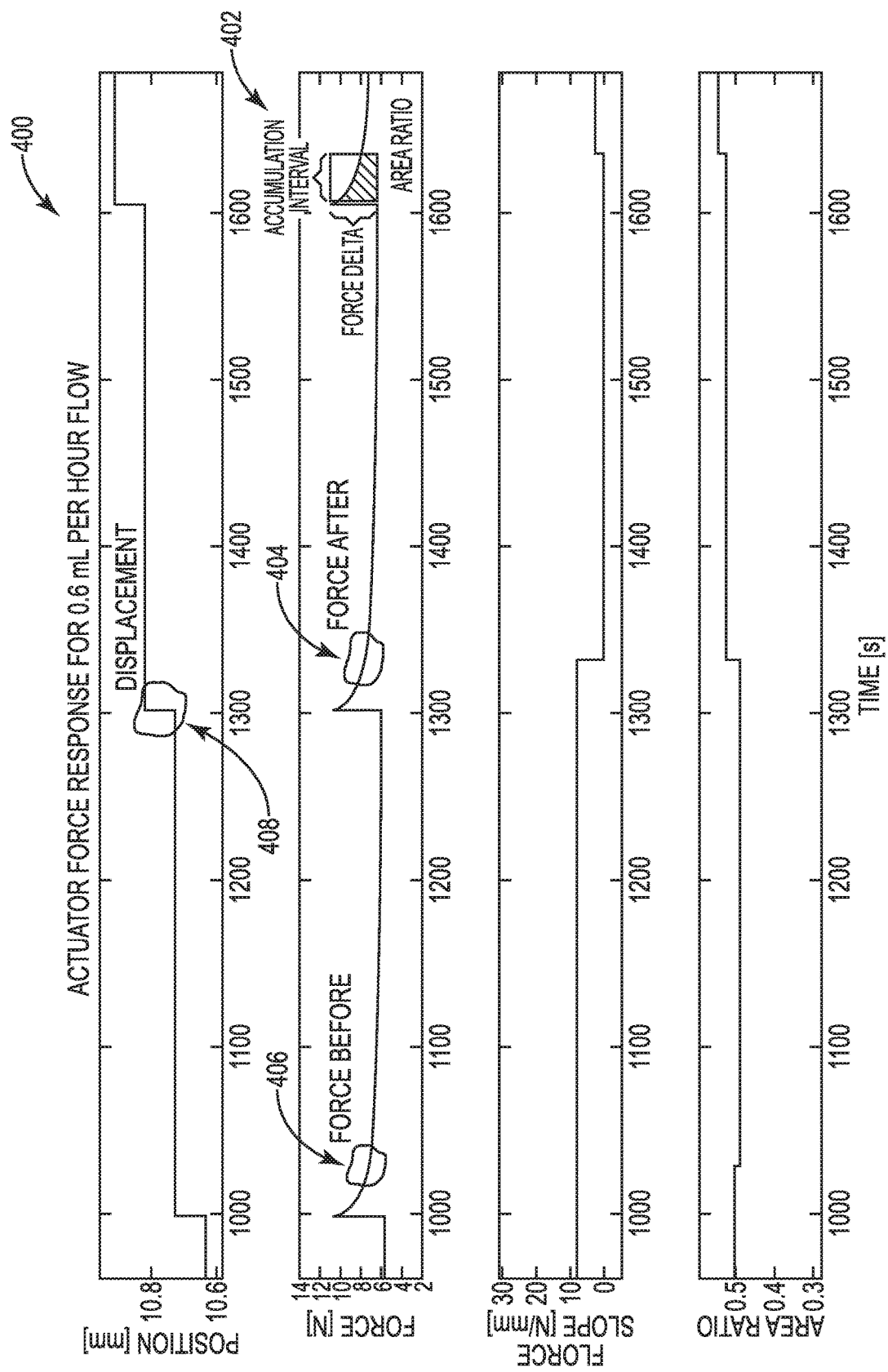
FIG. 9 is a graphical illustration of a force response and/or metrics thereof, for use in describing the exemplary algorithms for pressure priming of an infusion apparatus.

In other words, in one exemplary embodiment to determine whether the infusion line looks occluded (block 166), the controller 14 may be configured to calculate an area ratio as described herein, such as by determining an integrated force response value using integration of the force signal over a predetermined time period (e.g., a predetermined or set time period (t2−t1) as shown in FIG. 10 or the accumulation interval as shown in FIG. 9). As shown in FIG. 10, and described further herein, in one or more embodiments, the integrated force response value may be representative of area A1 or area A2. Further, the controller 14 may be configured to provide a ratio corresponding to the commanded bolus between the integrated force response value and a normalizing value. The normalizing value may be based on the maximum force of the measured force response. As shown in FIG. 10, and described further herein, the normalizing value may be representative of area A2 or area (A1+A2). Using the ratio for a commanded bolus, the controller 14 may determine if the infusion line appears occluded (e.g., whether the system is preventing the delivery of a bolus to one of the access blood line, the return blood line, and the patient when the infusion apparatus is commanded to do so). For example, it may be determined that infusion line looks occluded based on a comparison of the ratio corresponding to a bolus to a predetermined ratio indicative thereof (e.g., a threshold ratio that indicates the infusion line appears occluded, but rather, for example, a back pressure and/or frictional forces are merely preventing the delivery of a bolus).

As such, and with reference to FIG. 6 and decision block 166, a metric for determining whether the infusion line looks occluded may be an area ratio (e.g., a ratio as described herein, such as, area ratio A1/(A1+A2)) corresponding to a corresponding bolus. The ratio for that particular corresponding commanded bolus may be compared to a ratio threshold to determine whether the infusion line appears to be occluded. If no occlusion is indicated (block 166), then it is determined whether a predetermined number of boluses have been successfully delivered into the infusion line (e.g., using one or more metrics for each command). If it has been determined that a predetermined number of boluses have not yet been successfully delivered (block 168), then the infusion apparatus continues to be commanded to deliver boluses at the set flow rate and it continues to be determined whether the infusion line appears occluded for such commanded boluses (block 166). However, if it has been determined that a predetermined number of boluses have been successfully delivered to one of the access blood line, the return blood line, and the patient (block 168), then the infusion apparatus continues to be commanded to deliver boluses at the set flow rate (block 170) (e.g., no pressure priming is performed).

Another metric based on the measurable force response of commanded boluses that may be used alone or in combination with an area ratio to determine whether the infusion line looks occluded (block 166) is a force slope. For example, a measurable force signal representative of the measurable force response for each of at least two commanded boluses may be used to provide such a force slope value. The slope may be determined based on a force value taken at a predetermined time during each measurable force response for each of the at least two commanded boluses indicative of the stiffness of at least the replacement fluid dispenser (e.g., syringe). It may be determined whether the infusion line looks occluded (e.g., indicative of the system preventing boluses from being delivered by the infusion apparatus when commanded) based at least on such a force slope (e.g., a value that may be compared to a threshold).

FIG. 9 shows one or more illustrations relating to the force slope and area ratio metrics for use in determining whether an infusion line appears occluded when determining whether to provide pressure priming of a replacement fluid dispenser. FIG. 9 shows an example measurable force response profile (second graph from top) for three commanded micro-boluses and depicts the concept of one embodiment of an area ratio calculation therein.

For example, after the actuator is commanded to deliver a bolus and after the actuator stops moving and the measurable force response peaks, the area under the force curve is accumulated for a period of time (e.g., an accumulation time of 30 seconds) (see reference numeral 402). The particular area ratio calculated in this embodiment is the ratio of the area under the measurable force response curve (shown shaded in FIG. 9), divided by the area of the square (equatable to the area ratio A1/(A1+A2) described with reference to FIG. 10). This may be referred to as the force delta multiplied by the accumulation interval. In furtherance of the description herein that the accumulation time period may be adjusted, for heparin connections, the micro-boluses are at least 35 seconds apart at the set flow rate, and the area ratio calculation accumulation interval is set for 30 seconds (e.g., as such the accumulation period falls within the time interval between commands based on the set flow rate). For calcium connections, for example, the micro-bolus period between commands based on the set flow rate can be as short as 4.5 seconds. In such a case, the accumulation interval may be slightly less than the time between such micro-boluses. Each of the measurable force responses shown in FIG. 9 is indicative of the successful delivery of a bolus by the infusion apparatus when commanded.

FIG. 9 also indicates the exemplary data points for calculation of an exemplary force slope calculation which measures the stiffness of the installed fluid dispenser (e.g., syringe). For example, the force slope calculation is the change in force level between successive delivery of boluses (e.g., micro-boluses) divided by the displacement of the actuator for providing a bolus. The units of the force slope are in newtons per millimeter, which is a measure of stiffness similar to the measurement of a stiffness of a spring. The force slope calculation may be updated at the same time as an area ratio, and either one of the force slope and the area ratio may be used alone, or both metrics may be used in conjunction when diagnosing whether the bolus exited the syringe when commanded (e.g., to determine whether or not the infusion line looks occluded (block 166)).

The force slope calculation may be determined with use of force values taken at any predetermined time during the multiple measurable force responses used to make such a calculation (e.g., the forces used for the force slope calculation are taken at the same time during each of the measurable force responses). For example, as shown in the example of FIG. 9, the force 404 at the end of the accumulation interval of the second measurable force response (circled at the end of the second of the three measurable force responses shown in FIG. 9) minus the force 406 at the end of the previous accumulation interval of the first measurable force response (circled at the end of the first of the three measurable force responses shown in FIG. 9) is the difference in force used for the force slope calculation. This difference in force (e.g., taken at the predetermined time during each measurable force response for each of the two measurable force responses corresponding to commands to deliver boluses) is then divided by the displacement of the actuator 408 during the attempt at delivering the bolus (such displacement is circled in the position graph of FIG. 9). The resulting value is referred to as the force slope.

For example, force slope can be used to determine if an infusion line looks occluded because when the line is occluded or pressure is building to overcome downstream pressure (e.g., system back pressure) and the actuator displaces, the force on the syringe arm will increase in proportion to the distance displaced multiplied by the spring constant of the installed syringe. For all various syringe brands, the stiffness of an installed syringe may be greater 20 N per mm. This value may be the threshold used for diagnosing whether a micro-bolus was delivered or not. If fluid exits the syringe, then the stiffness of the system quickly diminishes as fluid flows, and the force slope will be less than 20 N per mm.

In one exemplary embodiment as shown and described with reference to FIG. 9, when using the area ratio to diagnose whether a bolus was delivered or not, the threshold may be 0.4; but only if the corresponding force slope exceeds 11 N per mm. The force slope qualifier may be needed, at least in one circumstance, because in some cases the force has not finished decaying to its steady state value after the 30 seconds accumulation interval. This is the case for the example in FIG. 9, where the area ratio is calculated to be 0.545 as shown in the bottom area ratio graph of FIG. 9, yet the line was not occluded. For example, in cases where the force decays to a steady state within 30 seconds, an area ratio value exceeding a 0.4 threshold is good indicator of occlusion given the exponential decay of the force profile. When the infusion line is clamped or the downstream system back pressure exceeds the syringe pressure, there may be cases where the area ratio calculation yields a result less than 0.4. In one or more of such cases, the force delta is high due to an abrupt spike in the force overshadowing the rise in force.

It will be recognized, that metrics calculated over one or more commanded boluses may be used (e.g., may be averaged) to determine if the infusion line looks to be occluded. For example, prior to pressure priming, it may be necessary for one to determine that the delivery of boluses from more than one command is being prevented (e.g., metrics corresponding to two or more commands for delivery of boluses may be needed to determine that pressure priming is needed). Further, for example, it will be recognized, that metrics calculated over one or more commanded boluses may be used (e.g., may be averaged) to determine if boluses are successfully being delivered. For example, prior to commanding the infusion apparatus to deliver boluses at the set flow rate, it may be necessary for one to determine that system back pressure is not preventing the delivery of multiple boluses resulting from multiple commands (e.g., metrics corresponding to two or more commands for delivery of boluses may be needed to determine that pressure priming is not needed).

The area ratio and force slope metrics may be used alone or in combination to determine if a command to the infusion apparatus has resulted in a bolus exiting the syringe. FIG. 9 shows graphs representative of these metrics for three measurable force responses corresponding to three commands to the infusion apparatus to deliver boluses into the infusion line; each of the commands resulting in a delivered bolus (e.g., one or more of the metrics being determined for each corresponding command to the infusion apparatus to determine if flow exited the syringe for the commanded last bolus). If flow did not exit the syringe, then pressure priming may be warranted. However, in one or more embodiments, one or more additional conditions as described herein may also need to be met, or each of such additional conditions may be used alone or in combination to determine if pressure priming is to be allowed.

For example, with further reference to FIG. 6, if, for example, the infusion line looks to be occluded (block 166) (e.g., based on one or more metrics), then prior to pressure priming, one or more connection conditions may need to be met before allowing pressure priming to occur (block 172). For example, the pressure of the replacement fluid dispenser (e.g., syringe) may be compared to one or more measurable pressures or to a predetermined pressure to determine if pressure priming should be allowed. Further, for example, a predetermined volume of the replacement fluid dispenser (e.g., a volume of the syringe reservoir) may be compared to a calculated volume that was expected to be delivered based at least on actuator displacement of an actuator of the infusion apparatus (e.g., the displacement being used for the calculation being the displacement since the time of connection of the syringe in the infusion apparatus) to determine if pressure priming should be allowed. For example, such displacement is shown in the top graph of FIG. 9. Such calculation is generally representative of whether the syringe actuator displacement exceeds a limit related to the volume of the syringe reservoir.

Figure 7:
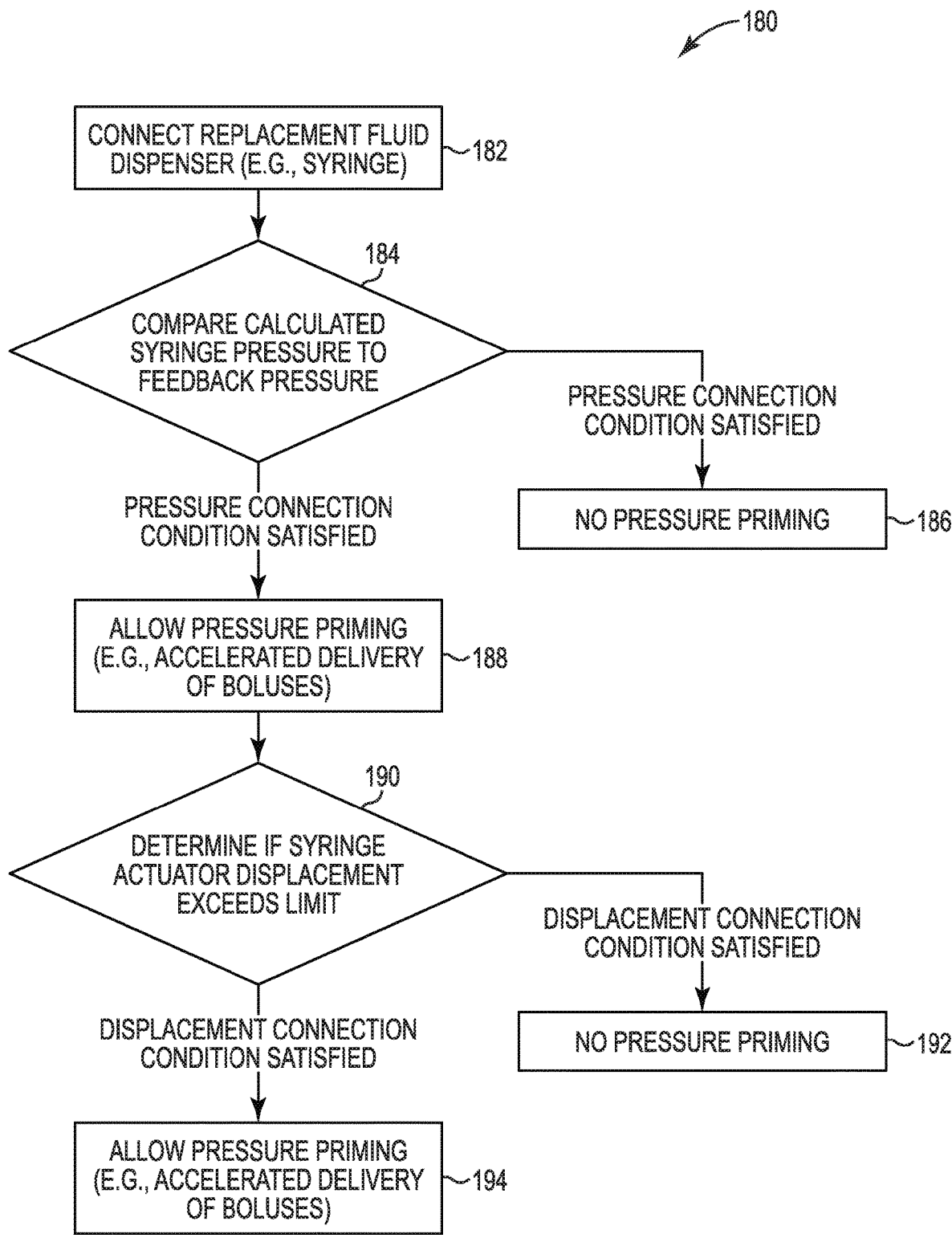
FIG. 7 is a block diagram illustrating another exemplary algorithm which may be used alone or in combination with one or more other algorithms described for pressure priming of an infusion apparatus for delivery of a fluid which may be implemented by a system, for example, such as shown generally in FIG. 3.

For example, FIG. 7 is a block diagram of a pressure priming algorithm 180 used to determine whether pressure priming should be allowed even if metrics indicate that the infusion line looks occluded (block 166). However, such connection conditions described herein may be used separately to determine whether pressure priming should be allowed and/or may be used in combination with one another, or may be used in combination with any one or more of the other metrics described herein (e.g., area ratio or force slope).

As shown in FIG. 7, with the replacement fluid dispenser connected in the infusion apparatus (block 182), a calculated replacement fluid dispenser pressure (e.g., estimated syringe pressure) may be compared to a feedback pressure to determine if pressure priming is to be allowed (block 184). The feedback pressure to which the estimated syringe pressure is to be compared is determined by the connection selected by the user at the time of setup. Such feedback pressure as previously described herein with reference to FIG. 4 may depend upon the user's selection during the initial setup 102. For example, if the connection chosen by the user is a heparin anticoagulant connection (e.g., infusion line connected pre-filter) then a pressure measurement at the input of the filter of the treatment system (e.g., filter 320 of system 310 of FIG. 3) may be made by a suitable pressure sensor (e.g., sensor 327 of FIG. 3) and used for determining whether to allow pressure priming (e.g., compared to the estimated syringe pressure). However, for example, if the connection chosen by the user is a citrate-based connection, and if the user has selected the connection of the infusion line for providing replacement calcium to the return line (e.g., region 604 in FIG. 11), then pressure measured in the return line of the treatment system (e.g., system 310 of FIG. 3) may be made by a suitable pressure sensor (e.g., transducer connected to port 329 of FIG. 3) and used for determining whether to allow pressure priming (e.g., compared to the estimated syringe pressure). Yet, still further, for example, if the connection chosen by the user is a citrate-based connection, and if the user has selected the connection of the infusion line for providing replacement calcium directly to the patient (e.g., region 602 in FIG. 11), then a predetermined pressure (e.g., a zero pressure) may be set and used for determining whether to allow pressure priming (e.g., compared to the estimated syringe pressure).

The syringe pressure may, as previously described herein, for example, be estimated using the force sensed at the syringe (e.g., the estimate of syringe pressure may be of: $P=7500.615*(F-4)/A$; where P is estimated syringe pressure in mmHg, F is sensed force in newtons (N), and A is the syringe cross sectional area in millimeters squared (cross sectional area of the barrel)). For example, if the comparison of the measured pre-filter pressure to the estimated syringe pressure meets certain pressure conditions, then pressure priming is allowed (block 188). However, if the comparison of the measured pre-filter pressure to the estimated syringe pressure does not meet certain pressure conditions, then pressure priming is not allowed (block 186).

For example, in heparin connection mode with the infusion line connected pre-filter, in one exemplary embodiment, the calculated syringe pressure estimate must not be more than 250 mmHg higher than the filter pressure to allow pressure priming to occur. For example, in calcium replacement connection mode where the infusion line is connected to the return line, the calculated syringe pressure estimate must not be more than 210 mmHg higher than the return pressure to allow pressure priming to occur. Further, for example, in a calcium replacement connection mode where the infusion line is connected directly to the patient, the calculated syringe pressure estimate must not be more than 210 mmHg to allow pressure priming to occur. In other words, the computed syringe pressure estimate must not exceed the measurable pressures (e.g., the return line pressure or the pressure at the inlet of the filter) by a certain pressure amount or when a measurable pressure is not available, such as in the case of the infusion line being connected directly to the patient, the computed syringe pressure estimate must not exceed a zero pressure (e.g., a predetermined pressure) by a certain pressure amount.

Yet further with reference to FIG. 7, with the replacement fluid dispenser connected in the infusion apparatus (block 162), it may be determined if the displacement of the actuator of the infusion apparatus exceeds certain limits (block 190), or in other words, whether such displacement satisfies certain connection conditions to determine if pressure priming should be allowed. For example, a predetermined volume of the replacement fluid dispenser (e.g., a volume of the syringe reservoir) may be compared to a calculated volume that was expected to be delivered based at least on actuator displacement of an actuator of the infusion apparatus (e.g., the displacement being used for the calculation being the displacement since the time of connection of the syringe in the infusion apparatus) to determine if pressure priming should be allowed. For example, if the comparison of the predetermined volume of the syringe reservoir to a calculated volume that was expected to be delivered based at least on actuator displacement meets certain conditions, then pressure priming is allowed (block 194). However, if the comparison does not meet certain conditions, then pressure priming is not allowed (block 192).

Such conditions may vary depending upon the connection selected by the user at the time of setup (e.g., user's selection during the initial setup 102). For example, in heparin connection mode with the infusion line connected pre-filter, in one exemplary embodiment, the calculated volume of fluid that was expected to be delivered based on actuator displacement since the last syringe change cannot be greater than a corresponding syringe volume of 1.7 mL to allow pressure priming to occur. For example, in calcium replacement connection mode where the infusion line is connected to the return line, the calculated volume of fluid that was expected to be delivered based on actuator displacement since the last syringe change cannot be greater than a corresponding syringe volume of 1.23 mL to allow pressure priming to occur. Further, for example, in a calcium replacement connection mode where the infusion line is connected directly to the patient, the calculated volume of fluid that was expected to be delivered based on actuator displacement since the last syringe change cannot be greater than a corresponding syringe volume of 0.68 mL to allow pressure priming to occur. In other words, in one or more embodiments, the calculated volume of fluid that was expected to be delivered based on actuator displacement since the last syringe change cannot exceed a corresponding syringe volume by a certain amount or pressure priming is not allowed.

Further with reference to FIG. 6, with the replacement fluid dispenser connected in the infusion apparatus (block 162), the set flow rate may also be used to determine if pressure priming should be allowed. For example, pressure priming becomes more beneficial when the set flow rate is lower. For example, if the set flow rate is high, then the time interval between commands to deliver pulses is short and the syringe pressure will increase and overcome the system back pressure within a time period that may be sufficiently short enough such that pressure priming (e.g., accelerating commands to the infusion apparatus) is unnecessary. However, if the set flow rate is low, then the time interval between commands to deliver pulses is relatively longer and the time for the syringe pressure to grow and overcome the system back pressure is undesirably long. Accelerating such commands to the infusion apparatus to deliver the boluses into the infusion line decreases this relatively longer time to overcome the system back pressure such that delivery of boluses into the infusion line are successful. For example, pressure priming may be beneficial where the time interval between commands provided to deliver boluses at the set flow rate is greater than 45 seconds as described herein.

As such, before pressure priming is allowed as shown in FIG. 6, the pressure priming algorithm 160, may determine if the set flow rate is a low flow rate less than a predetermined rate (block 174) (e.g., determine if the time interval between commands provided to deliver boluses at the set flow rate is greater than a predetermined time interval value). If the set flow rate is a low flow rate such that pressure priming is beneficial, then accelerating commands to the infusion apparatus may be performed (block 176). However, if the set flow rate is not a low flow rate, then even if the other metrics and/or conditions indicate the need for pressure priming such pressure priming may not be performed. For example, if pressure priming is not to be performed, then it may be determined if a predetermined number of boluses have been successfully delivered (block 168), and if they have, then the infusion apparatus continues to be commanded to deliver boluses at the set flow rate (block 170). Otherwise, if a predetermined number of boluses have not been successfully delivered, then the infusion apparatus is commanded to deliver another bolus (block 164) and the metrics and/or conditions for determining the need for pressure priming continue to be performed (e.g., block 166, 172, and 174).

Still further with reference to FIG. 6, if one or more metrics and/or conditions are met, pressure priming may be used. For example, such pressure priming may include accelerating the delivery of boluses (e.g., commanding delivery of boluses earlier than would otherwise be commanded delivered) (block 176). As described herein, the pressure priming algorithm 160 may operate to accelerate one or more commands to deliver boluses (block 176) in various manners. For example, the controller may provide for accelerating commands by commanding the infusion apparatus to operate at an accelerated flow rate higher than the set flow rate as described with reference to FIG. 5.

Further, as shown in FIG. 6, acceleration of commands to the infusion apparatus for delivery of boluses may be determined on a command by command basis. For example, after a command to the infusion apparatus to deliver a bolus is issued based on the set flow rate, and it is determined that one or more metrics indicate the need for pressure priming (blocks 166, 172, and/or 174), a command to the infusion apparatus to deliver a next bolus is accelerated; the command being provided at a time interval from the immediately preceding command that is less than the time interval as prescribed by the set flow rate. For example, if the time interval between commands at the set flow rate is 360 seconds, then the accelerated command may be delivered to the infusion apparatus at a time interval less than 360 seconds (e.g., 45 seconds). The period of time following the delivery of the accelerated command is monitored (e.g., the force is monitored to calculate metrics, take pressure measurements, etc.) to determine whether the accelerated command resulted in a successfully delivered bolus or whether the bolus was prevented from being delivered to one of the access blood line, the return blood line, and the patient (block 166). If it appears that the infusion line is still occluded (e.g., indicative of the system back pressure still preventing the bolus from being delivered from the syringe), then if none of the other required conditions prevent pressure priming, an accelerated command is again provided to the infusion apparatus to deliver a next bolus at a time interval from the immediately preceding command that is less than the time interval as prescribed by the set flow rate (e.g., 45 seconds). Such acceleration of commands may, for example, continue until the infusion line no longer looks to be occluded (and/or various other conditions do not prevent pressure priming) (blocks 166, 172, and/or 174) and a predetermined number of boluses have been successfully delivered to one of the access blood line, the return blood line, and the patient (blocks 168, 170) (e.g., as indicated by one or more metrics (block 166)).

Figure 8:
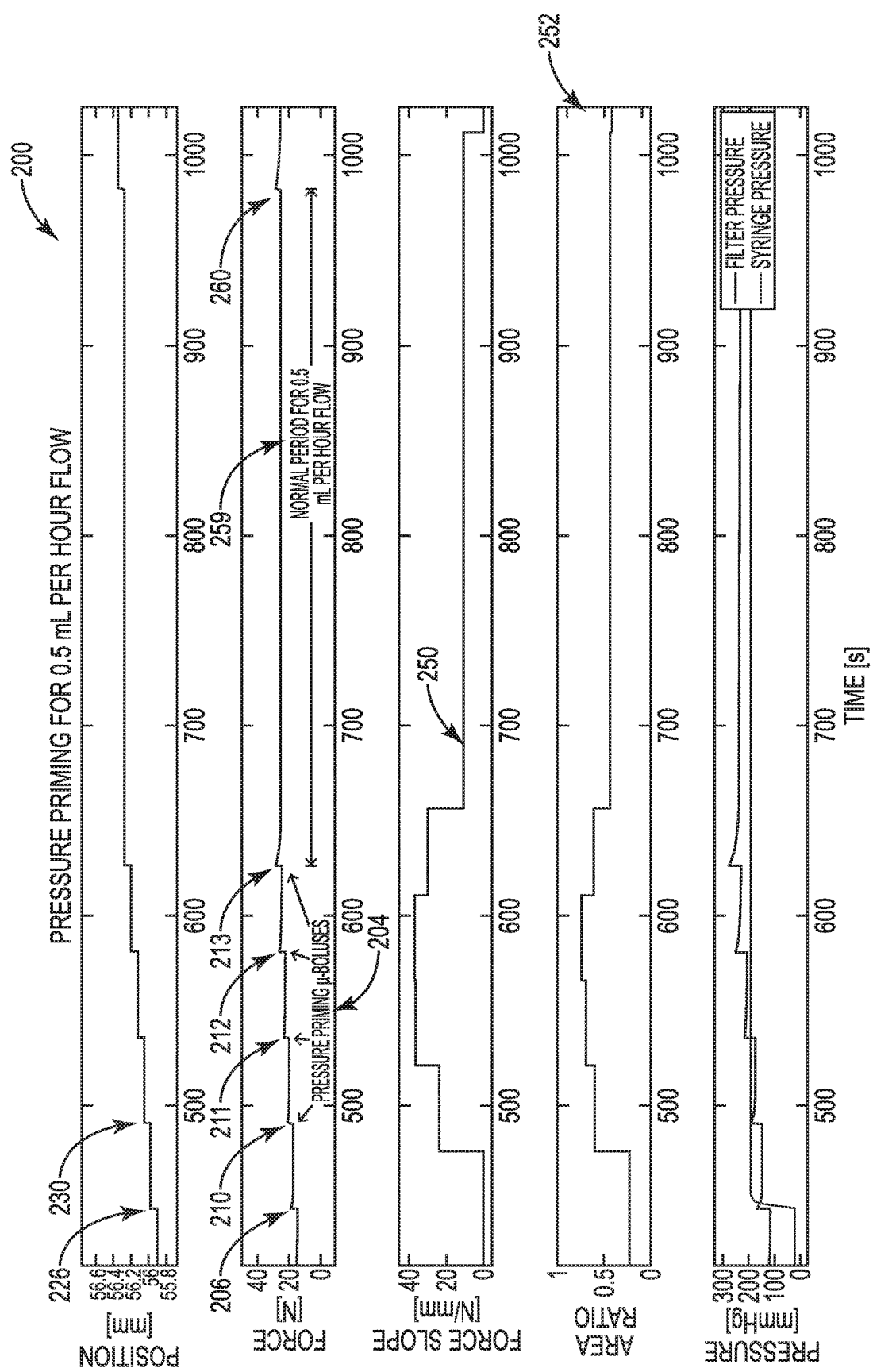
FIG. 8 is a graphical illustration of pressure priming for use in describing the exemplary algorithms for pressure priming of an infusion apparatus.

FIG. 8 shows a plurality of graphs 200 for illustrating an exemplary pressure priming algorithm. For example, in one exemplary blood treatment system in order for fluid to flow from a syringe when in heparin mode, the pressure in the syringe must exceed the filter pressure plus the cracking pressure of the one-way valve. The filter pressure can vary widely depending on the operating point of blood pump and fluid pumps in the system. Similarly, when in calcium mode and the infusion line is connected to the return line, the syringe pressure must exceed the return pressure. Pressure priming may be used to pressurize the syringe, after a syringe change, to the level of the filter or return pressure (e.g., depending on the connection mode) to achieve flow in a timely manner from the syringe.

In addition to achieving flow sooner after a syringe change employing pressure priming, an occluded line may be detectable sooner. For example, automatic pressure priming may be used to overcome false occlusion detections at low flows. For example, in one or more embodiments, there may be a requirement that occlusions be detected within set time frame (e.g., 20 minutes). At low flows, given the long duration between micro-pulses one could detect the equalization of the pressure phase (e.g., the syringe pressure rising to the level of the system back pressure) as occlusion. In at least one embodiment, since the pressure in the set is generally known where the syringe infusion line is connected) one can estimate the number of commanded boluses (e.g., pulses) one would need to deliver to pressurize the syringe to the system pressure and thus avoid false occlusion detections.

Pressure priming is particularly beneficial at low flow rates. The exemplary pressure priming algorithm can be simply stated as: for low flow rates, if a micro-bolus looks occluded (e.g., one or more metrics determined that the bolus is not successfully delivered) then do another micro-bolus at an accelerated rate (e.g., command the infusion apparatus to deliver a bolus 45 seconds after the last one rather than waiting the entire micro-bolus period dictated by the set flow rate) up to the point where flow is established.

FIG. 8 shows syringe pressure priming at the start of therapy. The filter pressure climbs to about 200 mmHg when the blood and fluid pumps start. The example shown in FIG. 8 relates to a low set flow rate of 0.5 mL with a time interval between commands for delivering boluses at this set flow rate being about 360 seconds. As such, after connection of a replacement syringe, a significant system back pressure operates on the syringe and prevents delivery of micro-boluses therefrom. The syringe controller commands four pressure priming micro-boluses (e.g., represented by the measurable force responses 204) to compensate and overcome the system back pressure such that micro-boluses are delivered to one of the access blood line, the return blood line, and the patient when commanded.

In operation, for example, upon command, the actuator of the infusion apparatus is displaced in an attempt to deliver a micro-bolus into the infusion line as indicated by the displacement labeled 226 in the top graph of FIG. 8. The measurable force response 206 corresponding to the command to deliver the bolus (e.g., the commanded bolus) is provided in the second graph from the top of FIG. 8. The metrics including force slope (as shown by the center graph of FIG. 8), area ratio (as shown by the graph directly above the lower graph on FIG. 8), and pressure (as shown in the lower graph on FIG. 8), are used to determine whether a bolus corresponding to the displacement 226 was successfully delivered into the infusion line. For example, with the force slope greater than 20, the area ratio greater than 0.4, and the pressure does not exceed the back pressure by more than 250 mmHg, it is determined that pressure priming should be carried out (e.g., such metrics were calculated in about 30 seconds).

As such, an accelerated command to deliver a bolus is provided about 45 seconds from the first command. The measurable force response 210 corresponding to the accelerated command is provided in the second graph from the top of FIG. 8. The actuator of the infusion apparatus is displaced in an attempt to deliver a micro-bolus into the infusion line as a result of the accelerated command as indicated by the displacement labeled 230 in the top graph of FIG. 8. The metrics including force slope, area ratio, and pressure, are used to determine whether a bolus corresponding to the displacement 230 was successfully delivered into the infusion line. For example, with the force slope greater than 20, the area ratio greater than 0.4, and the pressure does not exceed the back pressure by more than 250 mmHg, it is determined that pressure priming should continue to be carried out (e.g., such metrics were calculated in about 30 seconds).

As such, an accelerated command to deliver a bolus is provided about 45 seconds from the first accelerated command. A similar process is repeated with respect to the measurable force responses 211 and 212 corresponding to additional accelerated commands to the infusion apparatus (e.g., each command being provided about 45 seconds from the previous accelerated command).

However, the metrics calculated for the measurable force response 213 corresponding to an accelerated command as provided in the second graph from the top of FIG. 8, results in a determination that a micro-bolus was successfully delivered. For example, the metrics including force slope, area ratio, and pressure, were used to make such a determination. For example, with the force slope less than 20 (see reference numeral 250), the area ratio less than 0.4 (see reference 252), and the pressure above 200 mmHg, it is determined that pressure priming is no longer needed and the system back pressure has been overcome such that delivery of boluses will be successful. As such, the time interval for providing the next command to deliver a bolus into the infusion line reverts back to the time interval 259 dictated by the set flow rate (e.g., 360 seconds) as shown by the delivery of the next command corresponding to the measurable force response 260 in the second graph from the top of FIG. 8. The calculation of the syringe pressure, shown in the bottom graph, shows the syringe pressure building and overcoming the system back pressure operating on the syringe such that boluses are no longer being prevented from being delivered.

Still further, for example, the following exemplary logic may be used to decide whether to accelerate the flow rate (e.g., commands to deliver boluses) in another exemplary system to reach a pressure high enough to overcome downstream pressure in a timely manner. For example, after changing the syringe for a heparin connection, generally there is a mismatch between the syringe pressure and the filter pressure. When the filter pressure is near 400 mmHg, the syringe actuator may need to be displaced a certain amount (e.g., corresponding to an estimated delivery of as much as 1.0 mL) before the syringe pressure builds enough to overcome the filter pressure given typical syringe stiffness. Without pressure priming at 0.5 mL per hour flow rates, the time to overcome high filter pressures could be as much as two hours during which no fluid is actually delivered. In the meantime, if one does not account for the high filter pressure, the line will seem as though it is occluded. When the area ratio and force slope calculations suggest a micro-bolus was not delivered even though commanded, the periodic micro-bolus command is reissued at a 45 second mark rather than waiting the entire period for the next micro-bolus delivery (e.g., 360 seconds). A 45 second period is used so as to give the area ratio calculation sufficient data to complete, and also to prevent an over-reaction to the filter pressure reading, which may be in transient or conceivably incorrect. When the flow rate is 0.5 mL per hour, where the micro-boluses are 360 seconds apart, the duration of time saved each time the command is reissued is about 315 seconds. At this higher temporary rate of accelerating commands, the actuator displacement for a volume of 1 mL is less than 15 minutes as opposed to 2 hours, which builds enough pressure to overcome a worst case filter pressure, even though the continuous flow rate command is 0.5 mL per hour.

The pressure priming algorithm is particularly beneficial at low flow rates, e.g., less than 3.91 mL per hour, or where the period between micro-boluses is greater than 45 seconds. In many cases, at rates higher than this, the time it takes to overcome filter pressure without pressure priming by displacing 1.0 mL, if necessary, is approximately 15 minutes. As such pressure priming may not provide as great a benefit for the relatively higher set flow rates.

In one or more embodiments, pressure priming takes effect after a syringe change and lasts only until a predetermined number of boluses (e.g., 4 micro-boluses) have been diagnosed as successfully delivery from the syringe. Once several micro-boluses have been diagnosed as delivered, the syringe pressure has reached a steady operating point and pressure priming is no longer needed. For example, four micro-boluses may be used as the threshold, since in one or more embodiments, two micro-boluses may be diagnosed as delivered even though pressure is still building and no fluid is actually delivered. Additionally, another micro-bolus early in delivery is often misdiagnosed as delivered (e.g., perhaps because the syringe may slip in the syringe holder once the force on the syringe arm climbs high enough when building pressure).

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A blood treatment system comprising:
    a blood pump;
    a filter, wherein access and return blood lines are in fluid communication with the filter;
    an infusion line configured to be connected in fluid communication to one of the access blood line, the return blood line, and a patient;
    an infusion apparatus controllable to provide a fluid flow from a replaceable fluid dispenser at a set flow rate, wherein the fluid flow comprises a plurality of boluses, and further wherein the infusion apparatus comprises an actuator configured to operate on the replaceable fluid dispenser to provide one bolus of the plurality of boluses into the infusion line when commanded; and
    a controller configured to:
        determine, upon connection of a replacement fluid dispenser in the infusion apparatus, if the infusion apparatus is being prevented when commanded from delivering one or more boluses to one of the access blood line, the return blood line, and the patient, and
        prime the pressure in the replacement fluid dispenser if it is determined that the infusion apparatus is being prevented from delivering one or more boluses to one of the access blood line, the return blood line, and the patient, wherein the controller is configured to prime the pressure in the replacement fluid dispenser by accelerating one or more commands to the infusion apparatus to deliver one or more boluses into the infusion line so that pressure in the replacement fluid dispenser increases and a time required to deliver boluses to one of the access blood line, the return blood line, and the patient is decreased, wherein a time interval between an accelerated command and a prior command immediately preceding the accelerated command is less than a time interval between commands provided to deliver boluses at the set flow rate.

2. A method to control delivery of a fluid flow from an infusion apparatus in a blood treatment system, wherein the fluid flow comprises a plurality of boluses, wherein the method comprises:
    connecting a replacement fluid dispenser in the infusion apparatus to replace a prior replaceable fluid dispenser;
    commanding the infusion apparatus to operate on the replacement fluid dispenser to provide one or more boluses of the plurality of boluses into an infusion line configured to be connected in fluid communication to one of an access blood line, a return blood line, and a patient;
    determining if the infusion apparatus is being prevented when commanded from delivering the one or more boluses to one of the access blood line, the return blood line, and the patient;
    controlling the infusion apparatus to deliver a plurality of boluses at a set flow rate into the infusion line if the infusion apparatus is not being prevented from delivering the one or more boluses; and
    pressure priming the replacement fluid dispenser if the infusion apparatus is being prevented from delivering the one or more boluses by accelerating one or more commands to the infusion apparatus to deliver one or more boluses into the infusion line such that pressure in the replacement fluid dispenser increases and a time required to deliver boluses to one of the access blood line, the return blood line, and the patient is decreased, wherein a time interval between an accelerated command and a prior command immediately preceding the accelerated command is less than a time interval between commands provided to deliver boluses at the set flow rate.

3. The system of claim 1, wherein the controller is further configured to control the infusion apparatus to deliver a plurality of boluses at the set flow rate into the infusion line upon delivering a predetermined number of boluses resulting from accelerated commands to one of the access blood line, the return blood line, and the patient.

4. The system of claim 1, wherein the controller is further configured to increase the pressure in the replacement fluid dispenser by attempting to provide boluses at a rate greater than the set flow rate.

5. The system of claim 1, wherein determining whether the infusion apparatus is being prevented from delivering one or more boluses to one of the access blood line, the return blood line, and the patient comprises determining whether the infusion line appears occluded.

6. The system of claim 5, wherein each bolus is associated with a measurable force response over time, and further wherein determining whether the infusion line appears occluded is based on the measurable force response over time.

7. The system of claim 6, wherein determining whether the infusion line appears occluded comprises:
receiving a force signal representative of a measurable force response associated with a bolus;
determining an integrated force response value using integration of the force signal over a predetermined time period;
providing a ratio corresponding to the bolus between the integrated force response value and a normalizing value; and
determining if the infusion line appears occluded based at least on the ratio corresponding to the bolus.

8. The system of claim 6, wherein determining whether the infusion line appears occluded comprises:
receiving a force signal representative of a measurable force response for each of at least two boluses;
determining a slope based on a force value taken at a predetermined time during each measurable force response for each of the at least two boluses indicative of the stiffness of at least the replacement fluid dispenser; and
determining if the infusion line appears occluded based at least on the slope.

9. The system of claim 1, wherein the controller of the system is further configured to:
compare a calculated volume of fluid that was expected to be delivered based at least on actuator displacement of an actuator of the infusion apparatus since the time of connection of the replacement fluid dispenser in the infusion apparatus to a predetermined volume of the replacement fluid dispenser; and
prevent or allow pressure priming based on the comparison.

10. The system of claim 1, wherein the controller of the system is further configured to:
compare a pressure of the replacement fluid dispenser to at least one of a measurable pressure at an inlet of the filter, a measurable pressure of the return blood line, or a zero pressure; and
prevent or allow pressure priming based on the comparison.

11. The system of claim 1, wherein the controller of the system is further configured to:
command the infusion apparatus to attempt to deliver one or more boluses into the infusion line based on the set flow rate upon connecting the replacement fluid dispenser in the infusion apparatus,
wherein if it is determined that the infusion apparatus is not being prevented when commanded from delivering one or more boluses to one of the access blood line, the return blood line, and the patient then the infusion apparatus continues to be commanded to deliver further boluses as prescribed by the set flow rate, and
further wherein if it is determined that the infusion apparatus is being prevented when commanded from delivering the one or more boluses to one of the access blood line, the return blood line, and the patient then the infusion apparatus is commanded to deliver one or more boluses at an accelerated rate greater than the set flow rate.

12. The system of claim 1, wherein the controller of the system is further configured to:
command the infusion apparatus to deliver a bolus into the infusion line based on the set flow rate upon connecting the replacement fluid dispenser in the infusion apparatus,
wherein if it is determined that the infusion apparatus is not being prevented when commanded from delivering the bolus to one of the access blood line, the return blood line, and the patient then the infusion apparatus continues to be commanded to deliver further boluses at time intervals from immediately preceding boluses as prescribed by the set flow rate, and
further wherein if it is determined that the infusion apparatus is being prevented when commanded from delivering the bolus to one of the access blood line, the return blood line, and the patient then the infusion apparatus is commanded to accelerate a command to deliver a next bolus at a time interval from the immediately preceding command that is less than the time interval as prescribed by the set flow rate, wherein until a predetermined number of boluses have been delivered to one of the access blood line, the return blood line, and the patient accelerated commands continue to be provided to the infusion apparatus.

13. The system of claim 1, wherein the replacement fluid dispenser connected in the infusion apparatus is connected in the infusion apparatus upon determination that a replaceable fluid dispenser change was needed during operation of the blood treatment system.

14. The system of claim 1, wherein the set flow rate is a low infusion rate, wherein the time interval between commands provided to deliver boluses at the set flow rate is greater than 45 seconds.

15. The system of claim 1, wherein the time interval between an accelerated command and a prior command immediately preceding the accelerated command is equal to or less than ½ the time interval between commands provided to deliver boluses at the set flow rate.

16. The system of claim 15, wherein the time interval between an accelerated command and a prior command immediately preceding the accelerated command is equal to or less than ¼ the time interval between commands provided to deliver boluses at the set flow rate.

17. The system of claim 1, wherein the replacement fluid dispenser comprises a syringe.

18. The system of claim 1, wherein the infusion apparatus is configured to deliver an anticoagulant or a fluid used in combination with an anticoagulant.

19. A blood treatment system comprising:
a blood pump;
a filter, wherein access and return blood lines are in fluid communication with the filter;
an infusion line;

a user interface configured to allow a user to provide an input comprising a selected connection, wherein the selected connection comprises one of a connection of the infusion line to the return blood line or connection of the infusion line directly to a patient;

an infusion apparatus controllable to provide a fluid flow from a replaceable fluid dispenser at a set flow rate to the infusion line, wherein the fluid flow comprises a plurality of boluses; and a controller configured to:
determine, upon connection of a replacement fluid dispenser in the infusion apparatus and if the user provided a selected connection of the infusion line to the return blood line, whether the infusion apparatus is being prevented from delivering one or more boluses to the return blood line, and prime the pressure in the replacement fluid dispenser if it is determined that the infusion apparatus is being prevented from delivering one or more boluses to the return blood line.

20. The system of claim 19, wherein the controller is further configured to:
determine, upon connection of a replacement fluid dispenser in the infusion apparatus and if the user provided a selected connection of the infusion line to the patient, whether a frictional force associated with replacement fluid dispenser is preventing the infusion apparatus from delivering one or more boluses to the patient, and prime the pressure in the replacement fluid dispenser if it is determined that the frictional force associated with the replacement fluid dispenser is preventing the infusion apparatus from delivering one or more boluses to the patient.

21. The system of claim 19, wherein the replacement fluid dispenser comprises a syringe configured to deliver a fluid for use in combination with a citrate anticoagulant.

22. The system of claim 1, wherein the controller is further configured to determine, upon connection of a replacement fluid dispenser in the infusion apparatus, if a system back pressure operating on the replacement fluid dispenser and/or a frictional force associated with the replacement fluid dispenser is preventing the infusion apparatus when commanded from delivering one or more boluses to one of the access blood line, the return blood line, and the patient.

23. A treatment system comprising:
an infusion line;
an infusion apparatus controllable to provide a fluid flow from a replaceable fluid dispenser at a set flow rate downstream therefrom, wherein the fluid flow comprises a plurality of boluses, and further wherein the infusion apparatus comprises an actuator configured to operate on the replaceable fluid dispenser to provide one bolus of the plurality of boluses into the infusion line when commanded; and a controller configured to:
determine, upon connection of a replacement fluid dispenser in the infusion apparatus, if the infusion apparatus is being prevented when commanded from delivering one or more boluses downstream of the infusion apparatus, and prime the pressure in the replacement fluid dispenser if it is determined that the infusion apparatus is being prevented from delivering one or more boluses downstream of the infusion apparatus, wherein the controller is configured to prime the pressure in the replacement fluid dispenser by accelerating one or more commands to the infusion apparatus to deliver one or more boluses into the infusion line so that pressure in the replacement fluid dispenser increases and a time required to deliver boluses is decreased, wherein a time interval between an accelerated command and a prior command immediately preceding the accelerated command is less than a time interval between commands provided to deliver boluses at the set flow rate.

24. A method to control delivery of a fluid flow from an infusion apparatus, wherein the fluid flow comprises a plurality of boluses, wherein the method comprises:
connecting a replacement fluid dispenser in the infusion apparatus to replace a prior replaceable fluid dispenser;

commanding the infusion apparatus to operate on the replacement fluid dispenser to provide one or more boluses of the plurality of boluses into an infusion line;

determining if the infusion apparatus is being prevented when commanded from delivering the one or more boluses downstream of the infusion apparatus;

controlling the infusion apparatus to deliver a plurality of boluses at a set flow rate into the infusion line if the infusion apparatus is not being prevented from delivering the one or more boluses; and pressure priming the replacement fluid dispenser if the infusion apparatus is being prevented from delivering the one or more boluses by accelerating one or more commands to the infusion apparatus to deliver one or more boluses into the infusion line such that pressure in the replacement fluid dispenser increases and a time required to deliver boluses is decreased, wherein a time interval between an accelerated command and a prior command immediately preceding the accelerated command is less than a time interval between commands provided to deliver boluses at the set flow rate.

* * * * *